(12) United States Patent
Jezek et al.

(10) Patent No.: US 9,023,985 B2
(45) Date of Patent: May 5, 2015

(54) GLUCAGON COMPOSITION

(71) Applicant: Arecor Ltd., Cambridge (GB)

(72) Inventors: Jan Jezek, Cambridge (GB); Barry Kingston Derham, Cambridge (GB)

(73) Assignee: Arecor Ltd., Cambridge (GB)

( * ) Notice: Subject to any disclaimer, the term of this patent is extended or adjusted under 35 U.S.C. 154(b) by 0 days.

(21) Appl. No.: 13/834,313

(22) Filed: Mar. 15, 2013

(65) Prior Publication Data

US 2013/0252893 A1    Sep. 26, 2013

Related U.S. Application Data

(63) Continuation-in-part of application No. PCT/GB2011/052139, filed on Nov. 3, 2011.

(60) Provisional application No. 61/503,178, filed on Jun. 30, 2011, provisional application No. 61/503,104, filed on Jun. 30, 2011, provisional application No. 61/409,785, filed on Nov. 3, 2010, provisional application No. 61/409,723, filed on Nov. 3, 2010.

(51) Int. Cl.
    *A61K 38/26*      (2006.01)
    *C07K 14/605*      (2006.01)
    *A61K 47/18*      (2006.01)

(52) U.S. Cl.
    CPC .............. *A61K 47/186* (2013.01); *A61K 38/26* (2013.01)

(58) Field of Classification Search
    None
    See application file for complete search history.

(56) References Cited

U.S. PATENT DOCUMENTS

| | | | |
|---|---|---|---|
| 6,329,403 B1 * | 12/2001 | Odaka et al. | 514/342 |
| 2008/0029083 A1 * | 2/2008 | Masada et al. | 128/200.14 |
| 2011/0097386 A1 * | 4/2011 | Steiner et al. | 424/450 |

FOREIGN PATENT DOCUMENTS

| | | | | |
|---|---|---|---|---|
| EP | 0 199 992 A1 | 11/1986 | | |
| GB | 1 202 607 A | 8/1970 | | |
| WO | WO 99/24019 A1 | 5/1999 | | |
| WO | WO 99/47160 A1 | 9/1999 | | |
| WO | WO 2009/033738 A2 * | 3/2009 | | A61P 3/00 |
| WO | WO 2011/049713 A2 | 4/2011 | | |

OTHER PUBLICATIONS

Izutsu, Therapeutic proteins, methods and protocols, Humana press, edited by C. Mark Smales and David C. James, 2005, pp. 287-292.*
Sellers et al, Therapeutic proteins, methods and protocols, Humana press, edited by C. Mark Smales and David C. James, 2005, pp. 243-263.*
Definition of analogue, from http://cancerweh.ncl.ac.uk/cgi-hin/omd?analogue, pp. 1-5, accessed Jul. 7, 2005.*
Definition of variant, from http://www.merriam-webster.com/dictionary/variant, p. 1, accessed Sep. 30, 2013.*
Guest et al, Circular Dichroism Reveals Sensitivity of Glucagon Solution Structure to Fluoroalcohols, pH and Ionic Strength, Protein & Peptide Letters, 2008, 15, pp. 811-817.*
International Search Report for International Application PCT/GB2011/052139, European Patent Office, Netherlands, mailed Jan. 30, 2012.
Steiner, Solomon S., et al.,"Stabilized glucagon formulation for bihormonal pump use," *J. Diabetes Sci Technol*; 4(6):1332-1337; Diabetes Technology Society (Nov. 2010).

* cited by examiner

*Primary Examiner* — Julie Ha
*Assistant Examiner* — Li Ni Komatsu
(74) *Attorney, Agent, or Firm* — Sterne, Kessler, Goldstein & Fox P.L.L.C.

(57) ABSTRACT

There is provided according to the invention an aqueous composition having pH between 4 and 7 comprising (i) glucagon at a concentration of 0.05% w/v or more and (ii) a cationic surfactant selected from benzalkonium salts and benzethonium salts as solubilizing agent in an amount sufficient to dissolve the glucagon in the composition.

20 Claims, 8 Drawing Sheets

GLUCAGON COMPOSITION

CROSS-REFERENCE TO RELATED APPLICATIONS

This application is a continuation-in-part of PCT/GB2011/052139 filed on Nov. 3, 2011, which claims priority to U.S. Application No. 61/409,785 filed on Nov. 3, 2010, U.S. Application No. 61/409,723 filed on Nov. 3, 2010, U.S. Application No. 61/503,104 filed on Jun. 30, 2011 and U.S. Application No. 61/503,178 filed on Jun. 30, 2011. The entire teachings of the above applications are incorporated herein by reference.

FIELD OF THE INVENTION

This invention relates to formulations of glucagon and their use in therapy, particularly in rescue from hypoglycaemia.

BACKGROUND

Glucagon is a polypeptide hormone secreted by the alpha cells of the Islets of Langerhans in the pancreas. In native form it is a single chain polypeptide of 29 amino acid residues, the sequence of which is provided in Merck Index 10$^{th}$ Edition (1983).

Physiologically, glucagon plays a major role in the regulation of blood glucose levels and is involved in glyeogenolyic and gluconeogenetic effects. Due to its glycogenolytic effect on the liver, glucagon has become an established treatment of acute hypoglycaemia, including that caused by excessive insulin treatment in diabetics. In addition glucagon is known to exert a spasmolytic effect on smooth muscles which can also be exploited for therapeutic or diagnostic purposes, for example in imaging procedures.

Glucagon compositions for injection are currently marketed in the form of lyophilised powders for reconstitution with an aqueous medium, at a pH of 2-3, shortly before administration. It would be far more convenient in an emergency situation if glucagon could be provided in the form of an aqueous preparation such as an aqueous solution or aqueous gel, ready for immediate administration. Unfortunately hitherto attempts to develop such a formulation have foundered due to lack of solubility and instability of glucagon. A number of stability aspects affect glucagon in aqueous solutions, including aggregation, fibril formation and gel formation. In addition, glucagon undergoes deamidation of glutamine residues, particularly at and below pH 4 and at and above pH 7. Solubility of glucagon is generally improved at very low pH (pH<3). However, in such acidic compositions hydrolytic processes affect the stability of glucagon and such formulations also cause more pain on injection.

Nevertheless various aqueous formulations of glucagon have been proposed in the prior art.

GB1202607 claims a stable aqueous injectable glucagon solution which comprises glucagon in an amount of from 0.1 to 5 mg per ml together with a stabilising and solubilising amount of a surfactant. Anionic and cationic surfactants are described as being potentially suitable, and amongst cationic surfactants, quarternary ammonium bases in which at least one substituent is an aliphatic chain having at least 6 carbon atoms, preferably 12 to 20 carbon atoms, are preferred, especially cetrimide (cetyl trimethylammonium bromide).

WO99/47160 claims an aqueous glucagon solution comprising a stabilising and solubilising amount of a detergent having at least 2 positive charges, at least 2 negative charges, or a combination of at least one positive charge and one negative charge, the peptide being present in a concentration of at least about 0.1 mg/ml and with the proviso that the detergent is not dodecyl phosphocholine.

EP199992A1 (Eisai) describes use of benzethonium chloride and benzalkonium chloride in peptide compositions to prevent peptide adsorption onto plastic or glass. Although glucagon in mentioned in this context in very general terms in the description section, there is no working example with glucagon.

WO2011049713A2 (Biodel) discloses a stabilised glucagon formulation containing a surfactant, a mono or disaccharide, wherein the surfactant and saccharide are in an effective amount to staibilise the glucagon and wherein the osmolarity is approximately 200 to 400 mOs and the pH is between 2 and 8.

So far as we are aware none of these formulations has reached the marketplace.

We have now invented a novel glucagon formulation with a view to eliminating or mitigating some or all of the disadvantages of prior art formulations.

An objective of the invention is the provision of a formulation of glucagon which is adequately stable over a time period in storage or when carried by the patient in readiness for emergency use. Another objective of the invention is the provision of a formulation of glucagon which is adequately stable over a time period in storage and used in the prevention of hypoglycaemia or otherwise in the effective control of diabetes when administered to a patient also receiving treatment with insulin or an analogue of insulin.

SUMMARY OF THE INVENTION

Thus, according to the invention, there is provided an aqueous composition having pH between 4 and 7 comprising (i) glucagon at a concentration of 0.05% w/v or more and (ii) a cationic surfactant selected from benzalkonium salts and benzethonium salts as solubilising agent in an amount sufficient to dissolve the glucagon in the composition.

DETAILED DESCRIPTION OF THE INVENTION

Figure 1:
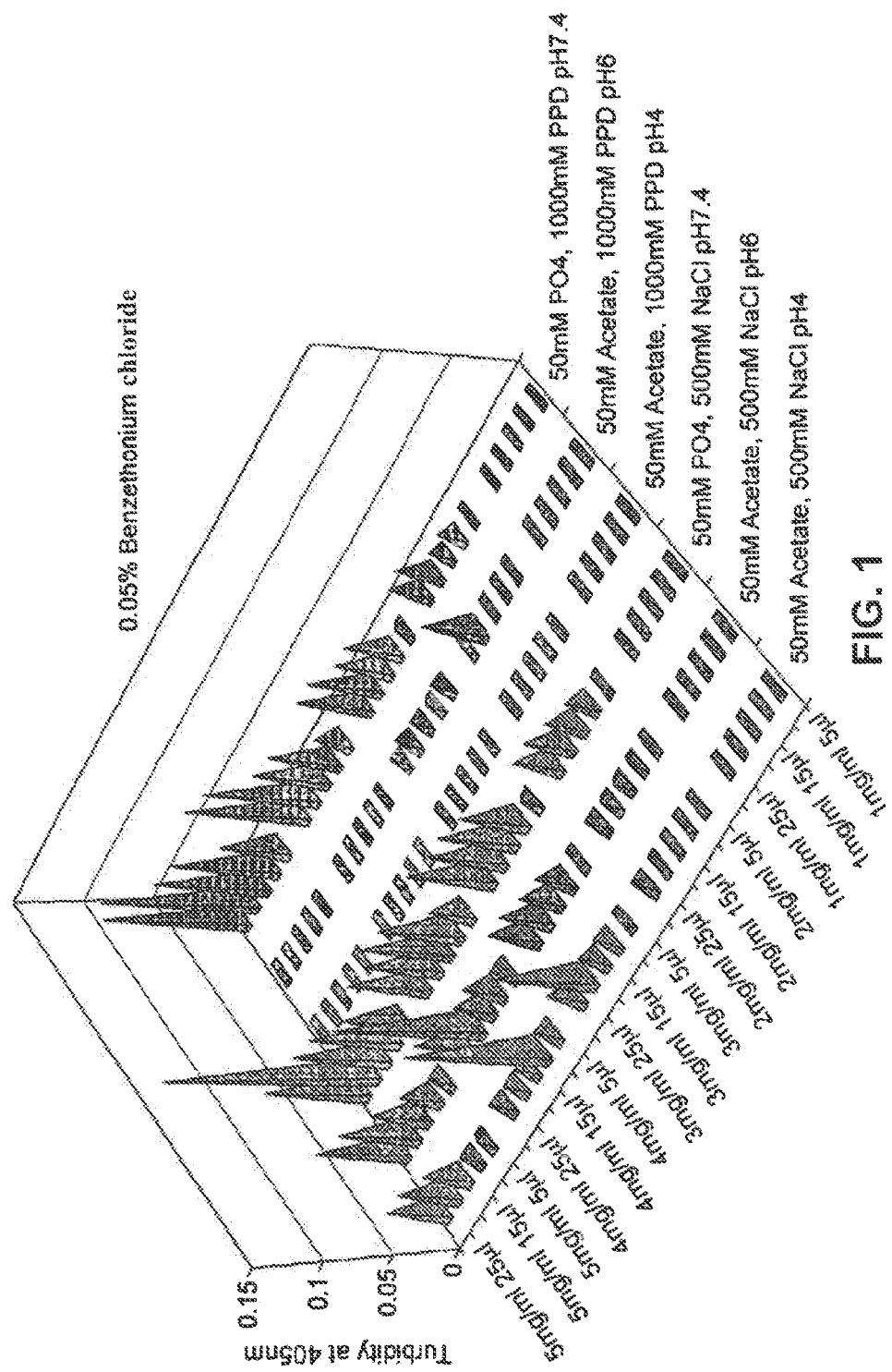
FIG. 1. Turbidity (405 nm) of aqueous compositions produced by mixing glucagon/Benzethonium solution with solutions A-F ((A) 50 mM acetate+500 mM NaCl (pH 4), (B) 50 mM acetate+500 mM NaCl (pH 6), (C) 50 mM phosphate+500 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+1000 mM 1,2-propanediol (pH 7.4)). Benzethonium chloride concentration was 0.05% (w/v).

As used herein "glucagon" means the polypeptide of 29 amino acids described in SEQ ID NO: 1 or an analogue or variant polypeptide having glucagon activity, specifically anti-hypoglycaemic activity. Specific variants include those polypeptides having a small number (e.g., 1, 2 or 3) of amino acid substitutions especially conservative substitutions relative to the sequence of SEQ ID NO: 1. Analogues also include polypeptides that comprise SEQ ID NO:1 or an aforementioned variant sequence. For example analogues include polypeptides consisting of SEQ ID NO:1 or an aforementioned variant sequence with an N and/or C terminal extension, typically a short extension for example of up to 10 amino acids e.g., up to 5 amino acids) at the N and/or C terminus.

Analogues also include derivatives of any of the aforementioned polypeptides such as derivatives designed to extend duration of action or blood residency such as derivatives involving attachment of one or more PEG moieties to the polypeptide (for example at One or more of amino acid positions 21 and 24 of glucagon), or attachment of fatty acid moieties (e.g., C4-C30 fatty: acids) by acylation or alkylation of one or more amino acids (for example the amino acid at position 10 of glucagon). Further analogues may involve incorporation of $\alpha,\alpha$-disubstituted acids e.g. aminoisobutyric acid for example at one, two, three or four of positions 16, 20, 21 and 24 of glucagon.

Exemplary glucagon analogues are described, in WO2010/011439, WO2009/155257, WO2009/155258, WO2009/099763, WO2009/058734, WO2009/058662, WO2008/101017, WO2008/086086 and WO2007/056362 all of which are herein incorporated by reference in their entirety.

In one embodiment the glucagon employed in the formulation has the sequence of SEQ ID NO:1.

Conservative substitutions of amino acids refer to the in of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; a group of amino acids having acidic side chains is aspartate and glutamate; and a group of amino acids having sulfur-containing side chains is cysteine and methionine. Substitutions within these groups may be regarded as conservative. Exemplary conservative amino acids substitution groups are valine-leucine/isoleucine, phenylalanine-tyrosine, lysine-arginine, alanine-valine, glutamate-aspartate, and asparagine-glutamine.

The pH of the composition is suitably 4.5-6.5, e.g., 5-6 or 4.5-5.5. Preferably it is around pH 5.5. Another suitable pH range is 6-7, e.g., 6-6.7 e.g., 6.1-7 e.g., 6-6.5 e.g., 6.1-6.5 or 6.5-6.7 or preferably 6.4-6.6. A composition at such a pH is typically not painful to inject and has adequate chemical stability of glucagon.

The concentration of glucagon may suitably be in the range 0.05 to 0.5% w/v (equivalent to 0.5-5 mg/ml). The concentration of glucagon may suitably be in the range 0.1 to 0.5% w/v, e.g., 0.1 to 0.2% w/v. Preferably it is 0.1% w/v.

In one embodiment the cationic surfactant is selected from benzethonium salts, e.g., benzethonium halide, especially the chloride. In another embodiment the cationic surfactant is selected from benzalkonium salts, e.g., benzalkonium halide, especially the chloride.

For example, the concentration of benzalkonium salt (based on benzalkonium chloride, but with a corresponding correction made for use of alternative anion) may be 0.001% to 0.05% w/v, e.g., 0.01% to 0.05% w/v (e.g., 0.01% to 0.03% w/v such as 0.01% to 0.025% w/v) or 0.005 to 0.015% w/v. Another range of possible interest is 0.05% to 0.20% w/v, e.g., 0.10% to 0.20 particularly 0.10% to 0.15% w/v or (less preferred) 0.15% to 0.20%.

For example, the concentration of benzethonium salt (based on benzethonium chloride, but with a corresponding correction made for use of alternative anion) may be 0.001% to 0.05% w/v, e.g., 0.01% to 0.05% w/v (e.g., 0.01% to 0.03% w/v such as 0.01% to 0.025% w/v) or 0.005 to 0.015% w/v. Another range of possible interest is 0.05% to 0.20% w/v, e.g., 0.10% to 0.15% w/v. Another possibility is 0.05% to 0.10 w/v or 0.15 to 020% w/v.

The composition may contain a mixture of a benzethonium salt and a benzalkonium salt. The combined concentration of the surfactants may in such case suitably be 0.001% to 0.05% w/v, e.g., 0.01% w/v, 0.05% w/v or 0.005 to 0.015% w/v. Another range of possible interest is 0.05 to 0.20% w/v, e.g., 0.10% to 0.15% w/v.

In the case of a solution it appears that a suitable concentration of benzalkonium salt or benzethonium salt is 0.05-0.20% w/v e.g., 0.15-0.20% w/v.

In the case of a gel it appears that a suitable concentration of benzalkonium salt or benzethonium salt is 0.001-0.05% w/v e.g., 0.01-0.05% w/v e.g., 0.01-0.03% w/v.

Suitably the composition contains said cationic surfactant in an amount wherein the ratio of concentration of glucagon/surfactant expressed as w/v is greater than 5/1 for example greater than 7/1 e.g., greater than 10/1 or greater than 25/1 or greater than 50/1.

In one embodiment the aqueous composition is a solution.

Suitably an aqueous composition of glucagon in the presence of benzethonium salt or benzalkonium salt according to the invention which is a solution remains as a clear solution during storage at 2-8° C. e.g., 4° C. for at least one year, preferably for at least two years. This means that no signs of visible precipitation, fibril formation or gel formation can be observed during storage. Suitably the aqueous composition of glucagon in the presence of benzethonium salt or benzalkonium salt according to the invention remains as a clear solution during storage at 25° C. for at least three months, preferably at least six months, more preferably for at least one year. This means that no signs of visible precipitation, fibril formation or gel formation can be observed during storage.

Thus suitably the solution is a clear solution with low viscosity (e.g., dynamic viscosity of less than 20 cP at 25° C.).

In another embodiment the aqueous composition is a gel especially a clear gel.

Suitably an aqueous composition of glucagon in the presence of benzethonium salt or benzalkonium salt according to the invention which is a gel remains as a clear gel during storage at 2-8° C. e.g., 4° C. for at least one year, preferably for at least two years. This means that no signs of visible precipitation or fibril formation can be observed during storage. Suitably the aqueous composition of glucagon in the presence of benzethonium salt or benzalkonium salt according to the invention remains as a clear gel during storage at 25° C. for at least three months, preferably at least six months, more preferably for at least one year. This means that no signs of visible precipitation or fibril formation can be observed during storage.

Irrespective of whether the composition is a liquid (solution) or a gel, suitably the proportion of chemically related species, e.g., deamidated or oxidised species, in the aqueous composition of glucagon in the presence of benzethonium salt or benzalkonium salt according to the invention remains below 25%, preferably below 10%, more preferably below 5% during storage at 2-8° C. e.g. 4° C. for at least three months, preferably for at least one year, more preferably for at least two years. For the purpose of minimising the formation of deamidated species, it can be preferable for the composition to be a gel.

Without being limited by theory, the reduced deamidation rate that apparently is a feature of the gel compositions as compared with the solution compositions of the invention may be attributed to reduced mobility of glucagon molecules in this physical state thereby reducing their propensity to deamidate by reaction of glutamine and asparagine residues with surrounding water molecules.

Suitably the formation of chemically related species, e.g., deamidated or oxidised species, in the aqueous composition of glucagon in the presence of benzethonium salt or benzalkonium salt according, to the invention remains below 25%, preferably below 10%, more preferably below 5% during storage at 25° C. for at least three months, preferably for at least one year. For the purpose of minimising the formation of deamidated species, it can be preferable for the composition to be a gel.

It may be convenient to test the compositions by performing accelerated stability studies at 40° C. Suitably the formation of chemically related species, e.g., deamidated or oxidised species, in the aqueous composition of glucagon in the presence of benzethonium salt or benzalkonium salt according to the invention remains below 25%, preferably below 10%, more preferably below 5% during storage at 40° C. for at least two months, preferably for at least six months.

Suitably the overall concentration of charged species in the composition is low. In the context of this invention, a charged species is defined a chemical entity which carries at least one charge under the conditions of the composition, e.g., sodium cation ($Na^+$), chloride anion ($Cl^-$) or an amino acid such as histidine. Suitably, the overall concentration of charged species, other than those originating from glucagon and the cationic surfactant, in the composition is less than 200 mM e.g., less than 150 mM e.g., less than 100 mM less than 50 mM e.g., less than 25 mM. In the inventors experience, this allows a lower concentration of the cationic surfactant to be used in order to solubilise the glucagon, whilst maintaining or even improving, its stability in solution.

In one embodiment the composition is substantially free of ionic species (apart from glucagon) which have a charge of more than 1. For example the composition is substantially free of ionic species (apart from glucagon) which have a charge of 2, 3, 4 or more.

Suitably the composition is substantially free of non-ionic surfactants such as TWEEN® 80, TWEEN® 20 and Pluronic surfactants.

Suitably the composition is substantially free of ionic surfactants including anionic, cationic and zwitterionic surfactants apart from a cationic surfactant selected from benzalkonium salts and benzethonium salts. For example suitably the composition is substantially free of surfactants selected from SDS, deoxycholate, cholate, stearate, phosphatidylcholine, CHAPS and cetrimide.

In this context "substantially free" means said ionic species or non-ionic or ionic surfactant is present at a concentration of less than 1 mM e.g. less than 0.1 mM e.g. less than 0.01 mM.

Suitably the composition is approximately isotonic. By "approximately isotonic" is meant a tonicity equivalent to that of around 130-170 mM NaCl, especially around 150 mM NaCl. Suitably the tonicity of the composition is maintained by inclusion of an uncharged tonicity modifying agent. Example uncharged tonicity modifying agents include polyols including sugars and sugar alcohols, for example selected from 1,2-propanediol, glycerol, mannitol, sorbitol, xylitol, lactitol, sucrose raffinose and trehalose, especially 1,2-propanediol or mannitol. Another suitable example is trehalose. It is desirable, but not essential, for the osmolarity of the composition to be in the range between 150-500 mOsm/l, preferably between 250-350 mOsm/l. When included, tonicity modifying agents are typically added at a concentration of 50-500 mM such as 100-300 mM e.g. 150-300 mM. For example 1,2-propanediol or mannitol may be added at a concentration of around 50-300 mM such as 100-300 mM e.g., 150-300 mM. In another example trehalose may be added at a concentration of around 50-500 mM such as 100-300 mM e.g., 150-300 mM. Preferably the uncharged tonicity modifying agent is mannitol or trehalose (or a mixture thereof), especially mannitol. In additional embodiments, trehalose is used as a mixture with 1,2-propanediol.

Suitably, the compositions (i.e., solutions, gels) of the invention comprise a buffer in order to stabilise the pH of the composition.

The buffer can also be selected to enhance protein stability. In one embodiment, a buffer is selected to have a pKa close to the pH of the composition; for example acetate is suitably employed as a buffer when the pH of the composition is in the range 4.5-5.5, for example at a concentration of 1 to 20 mM, such as 2 to 10 mM, e.g., at a concentration of around 5 mM. Alternatively, in another embodiment, the composition of the invention is further stabilised as disclosed in WO2008/084237, which describes a composition comprising a protein and one or more additives, characterised in that the system is substantially free of a conventional buffer, i.e., a compound with a $pK_a$ within unit of the pH of the composition at the intended temperature range of storage of the composition. In this embodiment, the pH of the composition is set to a value at which the composition has maximum measurable stability with respect to pH; the one or more additives (displaced buffers) are capable of exchanging protons with the protein, and have $pK_a$ values at least 1 unit more or less than the pH of the composition at the intended temperature range of storage of the composition. By keeping the protein at a suitable pH, at or near a value at which the measurable stability is maximal, in the absence of a conventional buffer, the storage stability of the protein can be increased substantially. In certain embodiments, storage stability can generally be enhanced further, possibly substantially, by use of additives having $pK_a$ between 1 to 5 pH units, preferably between 1 to 3 pH units, most preferably from 1.5 to 2.5 pH units, of the pH of the aqueous composition at the intended temperature range of storage of the composition, for example at 25° C. or at 2-8° C. e.g., 4° C. For example in one embodiment, acetate is employed as a displaced buffer when the pH of the composition is in a range 6-7. In additional embodiments, the concentration of acetate in the composition is 1 to 20 mM. In further embodiments, the concentration of acetate in the composition is 2 to 10 mM, such as, around 5 mM.

However the concentration of any buffer is suitably such that the concentration of charged ionic species in the composition is kept low, and most suitably within the ranges given above.

The compositions (i.e., solutions, gels) of the invention may also comprise an antioxidant in order to minimise the formation of oxidised species derived from glucagon. For example, the antioxidant is methionine or glutathione, e.g., used in a concentration of up to 5 mM e.g., 0.01 to 5 mM. In another example, butylated hydroxytoluene may be used in a concentration of op to 5 mM e.g., 0.01 to 5 mM. In particular embodiments, the compositions comprises methionine in an amount from 0.01 to 5 mM, e.g. 2 mM. In an alternative embodiment the compositions may be stored under an inert atmosphere, for example under nitrogen or argon, in order to minimise the formation of oxidised species derived from glucagon.

The solutions of the invention may also comprise phenol in order to further aid and maintain the solubilisation of glucagon. The amount of phenol may be up to 50 mM, for example 1 to 50 mM such as 5 to 30 mM e.g., 5 mM or 15 mM or 30 mM. In some embodiments, the amount of phenol is 10 mM or 20 mM or 25 mM. In particular embodiments, the solutions comprise phenol in an amount from 10 to 30 mM or from 15 to 25 mM.

A specific embodiment that may be envisaged is a composition according to the invention with a pH of around 5.5, comprising glucagon, benzethonium chloride as cationic surfactant, mannitol as tonicity modifying agent and acetate as buffer. There is also provided such a composition which additionally comprises methionine as antioxidant and/or phenol.

Another specific embodiment that may be envisaged is a composition according to the invention with a in the range 6.4-6.6, comprising glucagon, benzethonium chloride as cationic surfactant, trehalose as tonicity modifying agent. In some embodiments the composition further comprises 1,2-propanediol and/or phenol. In further embodiments, the composition comprises acetate as buffer. In additional embodiments, the composition additionally comprises methionine.

In some embodiments, the invention encompasses a composition that is a solution, with a pH in the range 6-7 (e.g., 6.1-7 and 6.4-6.6), comprising glucagon, benzethonium salt, a tonicity modifier, phenol, and acetate as buffer. In additional embodiments, the composition comprises methionine. In some embodiments the glucagon concentration is in the range 0.05 to 0.5% w/v (e.g., 0.1 to 0.5, 0.1 to 0.5, and 0.1 to 0.2% w/v). In a particular embodiment, the glucagon concentration is 0.1% w/v. In same embodiments, the benzethonium salt is benzethonium chloride at a concentration of 0.05 to 0.2% w/v (e.g., 0.1 to 0.15 and 0.15 to 0.2% w/v). In a particular embodiment, the benzethonium salt is benzethonium chloride at a concentration of 0.2% w/v. In some embodiments, the tonicity modifier is trehalose at a concentration of around 50-500 mM (e.g., 100-300 mM and 150-300 mM). In a particular embodiment, the tonicity modifier is a mixture of trehalose and 1,2-propanediol. In some embodiments, the composition contains phenol at a concentration of 1 to 50 mM (e.g., 10 to 30 mM and 15 to 25 mM). In additional embodiments, the composition contains methionine. In further embodiments, the composition contains methionine at a concentration of 0.01 to 5 mM (e.g., 2 mM). In some embodiments, the composition contains a buffer at a concentration of 1 to 20 mM (e.g., 2 to 10 mM). In further embodiments, the composition contains acetate as a buffer.

In a particular embodiment, the invention encompasses a composition that is a solution, with pH 6.1-7 (e.g., 6.4-6.6), comprising glucagon at a concentration of 0.1 to 0.2%, w/v (e.g., 0.1% w/v), a benzethonium salt (e.g., benzethonium chloride) at a concentration of 0.05 to 0.2% w/v (e.g., 0.2% w/v), one or more tonicity modifiers (e.g., trehalose and a mixture of trehalose and 1,2-propanediol) at a total concentration of 100-300 mM (e.g., trehalose at a concentration of 150-300 mM and 1,2-propane diol if present at a concentration of 50-250 mM) and a buffer (e.g., acetate) at a concentration of 1 to 20 mM (e.g. 2 to 10 mM). In some embodiments, the composition contains phenol at a concentration of 10 to 30 mM (e.g., 15 to 25 mM). In additional embodiments, the composition contains methionine at a concentration of 0.01 to 5 mM (e.g., 2 mM).

According to a further aspect of the invention there is provided use of a cationic surfactant selected from benzalkonium salts and benzethonium salts as solubilising agent tot glucagon in a composition as described herein. There is also provided a method of solubilising glucagon in an aqueous composition which comprises using a cationic surfactant selected from benzalkonium salts and benzethonium salts as solubilising agent in a composition as described herein.

There is also provided a method of treatment of hypoglycaemia which comprises administering to a subject suffering therefrom a therapeutically effective amount of a composition as described herein. There is also provided a composition as described herein for use as a pharmaceutical, especially for use in the treatment of hypoglycaemia. For example, said treatment of hypoglycaemia is treatment in an emergency setting. Alternatively, the composition as described herein is used in the prevention of hypoglycaemia or otherwise in the effective control of diabetes when administered to a patient also receiving treatment with insulin or an analogue of insulin, for example as disclosed in WO2004/060837A1 (Diobex) and WO2006/004696A2 (Diobex), both of which are herein incorporated by reference in their entirety.

An amount of glucagon which is suitable for administration as a single dose for treatment of hypoglycaemia is 1 mg for adults and 0.5 mg for juveniles. A corresponding volume of composition as described herein which is suitable for administration as a single dose for treatment of hypoglycaemia is 1 mL for adult and 0.5 mL for juveniles. A lower volume, higher concentration dose may also be suitable, e.g., 0.5 mL of a 2 mg/ml solution. The invention should not be considered to be limited to any such amount and other doses may be formulated according to the invention if appropriate.

There is also provided a container containing a unit dose of composition as described herein.

There is also provided a single-use injector for intramuscular, sub-cutaneous or parenteral administration comprising injection apparatus and a container containing a unit dose of composition as described herein to be injected.

For instance, the liquid composition of glucagon may be filled into a syringe (e.g., 1 mL syringe) composed of a staked-in needle, inert rubber stopper and plunger (e.g., polypropylene plunger). The syringe containing the product may optionally be housed into an autoinjector (assembled around the syringe) ready for automatic delivery of the required dose.

There is also provided a pump device such as a patch pump or infusion pump comprising a container in fluid communication with a needle containing a unit dose of composition as described herein to be injected or infused, and therefore adapted to inject or infuse such composition into a subject at a controlled rate.

Compositions according to the invention are expected to have the advantages of

Obviating the requirement for reconstitution and preparation of the required dose;
Facilitating rapid administration of the required dose which is essential for an emergency situation;
Reducing the incidence of administrating the wrong dose by the caregiver due to problems with using a syringe or reconstitution the dose fully;
In some embodiments, preventing needle stick injuries due to the needle being fully covered within the autoinjector; and
Improving the ease with which the product can be carried author used by the diabetic patient or by the caregiver of a diabetic patient.

Compositions according to the invention are expected to have good physical and chemical stability as described herein.

EXAMPLES

Example 1

Effect of Surfactants on the Solubility of Glucagon

Purpose of the Experiment

Glucagon is known to be soluble in aqueous solutions at pH<3 and >9. The solubility between pH 3 to 9 is extremely low. The purpose of this experiment was to assess the effect of various excipients, particularly surfactants, on the solubility of glucagon at pH around 6. The excipients were tested at a selected concentration as indicated and no experiments were carried out at this stage to explore the effect of the concentration of the excipients on the glucagon solubility. The concentration of excipients tested was in excess of that of glucagon.

Experimental Procedure

Approximately 2 mg of glucagon was weighed out into a glass vial and the solution of excipients was added to give final glucagon concentration of 1 mg/ml. Visual observations were made for up to 1 hour. All experiments except sodium deoxycholate contained 10 mM histidine buffer (pH 6). Sodium deoxycholate was formulated in 10 mM TRIS (pH 7.5) as deoxycholate itself forms a gel at pH<7.

Results

The solubility of glucagon is indicated in the table below

| Excipient | Concentration | | Glucagon solubility |
|---|---|---|---|
| Cetrimide** | 0.125% | (w/v) | Completely dissolved |
| Benzethonium chloride | 0.2% | (w/v) | Completely dissolved |
| Benzalkonium chloride | 0.2% | (w/v) | Completely dissolved |
| Potassium benzoate** | 20 | mM | Not dissolved |
| CHAPS** | 10 | mM | Completely dissolved |
| TWEEN® 20** | 2% | (w/v) | Completely dissolved |
| TWEEN® 80** | 2% | (w/v) | Not dissolved |
| TWEEN® 40** | 2% | (w/v) | Partially, but not completely dissolved |
| TWEEN® 80** | 2% | (w/v) | Not dissolved |
| Pluronic P-65** | 2% | (w/v) | Not dissolved |
| Pluronic P-68** | 2% | (w/v) | Not dissolved |
| Pluronic P-127** | 2% | (w/v) | Not dissolved |
| Tryptophan** | 10 | mM | Not dissolved |
| Methionine** | 50 | mM | Not dissolved |
| Sodium cholate** | 10 | mM | Not dissolved |
| Sodium deoxycholate** | 10 | mM | Completely dissolved* |
| Phosphatidylcholine** | 10 | mM | Phosphatidylcholine found to form very opaque solution itself, so not tested with glucagon |
| Sodium stearate** | 10 | mM | Sodium stearate found very scarcely soluble itself, so not tested with glucagon |
| Sorbitan monopalmitate** | 5 | mM | Not dissolved |
| SPAN 20** | 5 | mM | Cloudy solution in the presence of glucagon |

*Tested at pH 7.5 (with 10 mM TRIS buffer) as deoxycholate itself forms gel at pH < 7.
**reference excipients From the table above, it can be seen that there are several excipients capable of dissolving glucagon at near-neutral pH. These are:
Cetrimide (cationic surfactant)
Benzethonium chloride (cationic surfactant)
Benzalkonium chloride (cationic surfactant)
CHAPS (zwitterionie surfactant)
TWEEN® 20 (non-ionic surfactant)
Sodium deoxycholate surfactant), only at pH>7.5

Stability of glucagon in these surfactants was assessed by RP-HPLC. It was shown that no significant changes in the native form of glucagon were observed in the presence of the cationic surfactants (cetrimide, benzethonium, benzalkonium) and in the presence of deoxycholate after incubation at room temperature for days. In contrast, the size of the native peak diminished in the case of CHAPS to <10%) and in the case of TWEEN® 20 (to about 60%).

It was also shown that glucagon dissolved in deoxycholate had a tendency to form gels following incubation at room temperature, even though the sample was liquid immediately after preparation at pH 7.5. Formulating at pH>8 minimized the gel formation.

On the basis of this information the Inventors selected benzalkonium and benzethonium salts for further evaluation.

Example 2

A Matrix Approach to Investigate the Effect of Several Parameters on Glucagon Solubility and Appearance of the Dissolved Glucagon Purpose of the Experiment In this experiment, the combined effect of the following parameters was investigated on the solubility and appearance:
Nature of surfactant (benzethonium salt, benzalkonium salt)
Concentration of surfactant
pH
Concentration of ionic species
Experimental Procedure Forty solutions containing a given concentration of glucagon and a given concentration of a cationic surfactant were prepared. All solutions contained 2 mM acetate and were adjusted to pH 5. No additional excipients were present. The concentrations of glucagon and cationic surfactant are shown in the Table below together with the indication of glucagon solubility following incubation for 24 hours:

|  | Glucagon concentration | | | | |
| --- | --- | --- | --- | --- | --- |
| Surfactant | 1 mg/ml | 2 mg/ml | 3 mg/ml | 4 mg/ml | 5 mg/ml |
| Benzethonium chloride (0.05% w/v) | Dissolved | Dissolved | Dissolved | Dissolved | Dissolved |
| Benzethonium chloride (0.025% w/v) | Dissolved | Dissolved | Dissolved | Dissolved | Dissolved |
| Benzethonium chloride (0.01% w/v) | Dissolved | Dissolved | Dissolved | Dissolved | Dissolved |
| Benzethonium chloride (0.005% w/v) | Dissolved | Dissolved | Dissolved | Dissolved | Dissolved |
| Benzalkonium chloride (0.05% w/v) | Dissolved | Dissolved | Dissolved | Dissolved | Dissolved |
| Benzalkonium chloride (0.025% w/v) | Dissolved | Dissolved | Dissolved | Dissolved | Dissolved |
| Benzalkonium chloride (0.01% w/v) | Dissolved | Dissolved | Dissolved | Dissolved | Dissolved |
| Benzalkonium chloride (0.005% w/v) | Dissolved | Dissolved | Dissolved | Dissolved | Dissolved |

In addition, the following six aqueous solutions were prepared:

| Solution identifier | Composition |
| --- | --- |
| A | 50 mM acetate + 500 mM NaCl (pH 4) |
| B | 50 mM acetate + 500 mM NaCl (pH 6) |
| C | 50 mM phosphate + 500 mM NaCl (pH 7.4) |
| D | 50 mM acetate + 1000 mM 1,2-propanediol (pH 4) |
| E | 50 mM acetate + 1000 mM 1,2-propanediol (pH 6) |
| F | 50 mM phosphate + 1000 mM 1,2-propanediol (pH 7.4) |

Each of the solutions A-F were added in a step-wise manner to each of the glucagon/surfactant solutions as follows: 80 µl of the glucagon/surfactant solution was placed in a well on a 96-well plate and solution selected from A-F was added in five separate 5 µl aliquots (i.e., total of 25 µl added). The solution resulting from each 5 µl addition was mixed and allowed to equilibrate for 10 minutes. Visual assessment was then made and turbidity was measured at 405 nm.

So, after each 5 µl addition of the solution selected from A-F to the glucagon/surfactant solution, a composition of particular pH and concentration of various species was generated. The observations made thus demonstrate the solubility and visual appearance of glucagon in a large number of aqueous compositions containing a range of surfactant concentrations, pH and concentration of ionic species. After the last 5 µl addition the compositions were approximately isotonic. The concentrations of the solution components after each 5 µl addition are shown in the Table below:

| Added volume (µl) | 0 | 5 | 10 | 15 | 20 | 25 |
| --- | --- | --- | --- | --- | --- | --- |
| Total volume (µl) | 80 | 85 | 90 | 95 | 100 | 105 |
| Buffer, i.e., acetate or phosphate (mM) | 0 | 2.9 | 5.6 | 7.9 | 10.0 | 11.9 |
| NaCl (mM) | 0 | 29.4 | 55.6 | 78.9 | 100.0 | 119.0 |
| 1,2-Propanediol (mM) | 0 | 58.8 | 111.1 | 157.9 | 200.0 | 238.1 |
| Glucagon (mg/ml) | 1 | 0.94 | 0.89 | 0.84 | 0.80 | 0.76 |
|  | 2 | 1.88 | 1.78 | 1.68 | 1.60 | 1.52 |
|  | 3 | 2.82 | 2.67 | 2.53 | 2.40 | 2.29 |

-continued

|  | 4 | 3.76 | 3.56 | 3.37 | 3.20 | 3.05 |
|---|---|---|---|---|---|---|
|  | 5 | 4.71 | 4.44 | 4.21 | 4.00 | 3.81 |
| Surfactant (% w/v) | 0.05 | 0.047 | 0.044 | 0.042 | 0.040 | 0.038 |
|  | 0.025 | 0.024 | 0.022 | 0.021 | 0.020 | 0.019 |
|  | 0.01 | 0.0094 | 0.0089 | 0.0084 | 0.0080 | 0.0076 |
|  | 0.005 | 0.0047 | 0.0044 | 0.0042 | 0.0040 | 0.0038 |

Results

All original glucagon/surfactant solutions were fully dissolved and did not show signs of gel formation. Following the step-wise additions of the solutions A-F, some compositions showed signs of precipitation and/or gel formation. The results are shown in Tables 1-8 and FIGS. 1-8.

The Tables which are present below show the results of visual assessments:

TABLE 1

Visual assessment of aqueous compositions produced by mixing glucagon/Benzethonium solution with solutions A-F. Benzethonium chloride concentration was 0.05% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 5 µl | 5 mg/ml | 1 | 1 | 2* | 1 | 1 | 2* |
|  | 4 mg/ml | 1 | 1 | 2* | 1 | 1 | 2* |
|  | 3 mg/ml | 1 | 1 | 1 | 1 | 1 | 1 |
|  | 2 mg/ml | 1 | 1 | 1 | 1 | 1 | 1 |
|  | 1 mg/ml | 1 | 1 | 1 | 1 | 1 | 1 |
| 10 µl | 5 mg/ml | 1 | 1.5 | 2* | 1 | 1 | 2* |
|  | 4 mg/ml | 1 | 1 | 2* | 1 | 1 | 2* |
|  | 3 mg/ml | 1 | 1 | 2* | 1 | 1 | 2* |
|  | 2 mg/ml | 1 | 1 | 1.5 | 1 | 1 | 1 |
|  | 1 mg/ml | 1 | 1 | 1 | 1 | 1 | 1 |
| 15 µl | 5 mg/ml | 1 | 1.5 | 2.5* | 1 | 1 | 3* |
|  | 4 mg/ml | 1 | 1.5 | 2* | 1 | 1 | 2* |
|  | 3 mg/ml | 1 | 1 | 2* | 1 | 1 | 2* |
|  | 2 mg/ml | 1 | 1 | 1.5 | 1 | 1 | 1.5 |
|  | 1 mg/ml | 1 | 1 | 1.5 | 1 | 1 | 1 |
| 20 µl | 5 mg/ml | 1.5 | 2* | 3* | 1 | 1 | 3* |
|  | 4 mg/ml | 1.5 | 1.5 | 2* | 1 | 1 | 2.5* |
|  | 3 mg/ml | 1.5 | 1.5 | 2* | 1 | 1 | 2* |
|  | 2 mg/ml | 1 | 1 | 1.5 | 1 | 1 | 1.5 |
|  | 1 mg/ml | 1 | 1 | 1.5 | 1 | 1 | 1 |
| 25 µl | 5 mg/ml | 1.5 | 2* | 3* | 1 | 1 | 3* |
|  | 4 mg/ml | 1.5 | 1.5 | 3* | 1 | 1 | 3 |
|  | 3 mg/ml | 1.5 | 1.5 | 2* | 1 | 1 | 2* |
|  | 2 mg/ml | 1 | 1 | 1.5 | 1 | 1 | 1.5 |
|  | 1 mg/ml | 1 | 1 | 1.5 | 1 | 1 | 1 |

Conclusion from the Experiment Described in Table 1:

The visual observations shown in Table 1 demonstrate that the solubility of glucagon in the presence of benzethonium chloride (0.038-0.050% w/v concentration covered during the experiment) is compromised at pH 7.4. This observation was made in compositions of both high and low ionic strength, with the higher ionic strength compositions showing greater tendency to precipitate. Compositions at pH 6 and particularly at pH 4 showed much lower tendency to precipitate. However, the best compositions contained an uncharged component as the key tonicity modifier and these remained clear across the concentration ranges investigated in this experiment. Corresponding compositions with NaCl as the key tonicity modifier showed much greater tendency to precipitate, especially in the presence of higher concentration of glucagon. Glucagon precipitation was typically accompanied by an apparent increase in viscosity of the samples (gel formation), particularly in the higher ionic strength compositions.

TABLE 2

Visual assessment of aqueous compositions produced by mixing glucagon/Benzalkonium solution with solutions A-F. Benzalkonium chloride concentration was 0.05% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 5 µl | 5 mg/ml | 1 | 1.5* | 1.5* | 1 | 1 | 1 |
|  | 4 mg/ml | 1 | 1.5 | 1.5 | 1 | 1 | 1 |
|  | 3 mg/ml | 1 | 1 | 1.5 | 1 | 1 | 1 |
|  | 2 mg/ml | 1 | 1 | 1 | 1 | 1 | 1 |
|  | 1 mg/ml | 1 | 1 | 1 | 1 | 1 | 1 |
| 10 µl | 5 mg/ml | 1.5 | 2* | 2* | 1 | 1 | 1.5* |
|  | 4 mg/ml | 1.5 | 1.5 | 1.5* | 1 | 1 | 1.5* |
|  | 3 mg/ml | 1 | 1 | 1.5 | 1 | 1 | 1.5 |
|  | 2 mg/ml | 1 | 1 | 1 | 1 | 1 | 1 |
|  | 1 mg/ml | 1 | 1 | 1 | 1 | 1 | 1 |
| 15 µl | 5 mg/ml | 1.5 | 2* | 2.5* | 1 | 1 | 2* |
|  | 4 mg/ml | 1.5 | 1.5* | 2* | 1 | 1 | 2* |
|  | 3 mg/ml | 1 | 1 | 1.5 | 1 | 1 | 1.5 |
|  | 2 mg/ml | 1 | 1 | 1 | 1 | 1 | 1.5 |
|  | 1 mg/ml | 1 | 1 | 1 | 1 | 1 | 1 |
| 20 µl | 5 mg/ml | 1.5* | 2* | 3* | 1 | 1 | 2* |
|  | 4 mg/ml | 1.5* | 2* | 2.5* | 1 | 1 | 2* |
|  | 3 mg/ml | 1.5 | 1.5 | 2 | 1 | 1 | 1.5 |
|  | 2 mg/ml | 1 | 1 | 1.5 | 1 | 1 | 1.5 |
|  | 1 mg/ml | 1 | 1 | 1 | 1 | 1 | 1 |
| 25 µl | 5 mg/ml | 1.5* | 2.5* | 3* | 1 | 1 | 2.5* |
|  | 4 mg/ml | 1.5* | 2* | 2.5* | 1 | 1 | 2.5* |
|  | 3 mg/ml | 1.5 | 1.5 | 2 | 1 | 1 | 2 |
|  | 2 mg/ml | 1 | 1 | 1.5 | 1 | 1 | 1.5 |
|  | 1 mg/ml | 1 | 1 | 1 | 1 | 1 | 1 |

Conclusion from the Experiment Described in Table 2:

The conclusions which may be drawn from Table 2 (using benzalkonium) are very similar to those made above for similar compositions containing the same concentration of benzethonium. Clear, non-viscous compositions of glucagon across a wide concentration range could be prepared at pH 4 and pH 6 and the best compositions used an uncharged tonicity modifier. Increasing pH and ionic strength impairs the solubility of glucagon in benzalkonium-based compositions. Gel formation could also be observed in many of the precipitated samples.

TABLE 3

Visual assessment of aqueous compositions produced by mixing glucagon/Benzethonium solution with solutions A-F. Benzethonium chloride concentration was 0.025% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 5 µl | 5 mg/ml | 1 | 1 | 1.5 | 1 | 1 | 1.5 |
|  | 4 mg/ml | 1 | 1 | 1.5 | 1 | 1 | 1.5 |
|  | 3 mg/ml | 1 | 1 | 1.5 | 1 | 1 | 1.5 |
|  | 2 mg/ml | 1 | 1 | 1.5 | 1 | 1 | 1.5 |
|  | 1 mg/ml | 1 | 1 | 1 | 1 | 1 | 1 |

TABLE 3-continued

Visual assessment of aqueous compositions produced by mixing glucagon/Benzethonium solution with solutions A-F. Benzethonium chloride concentration was 0.025% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 10 μl | 5 mg/ml | 1.5* | 1.5* | 2* | 1 | 1 | 2* |
|  | 4 mg/ml | 1.5* | 1.5* | 2* | 1 | 1 | 2* |
|  | 3 mg/ml | 1.5* | 1.5* | 1.5* | 1 | 1 | 1.5* |
|  | 2 mg/ml | 1 | 1 | 1.5 | 1 | 1 | 1.5 |
|  | 1 mg/ml | 1 | 1 | 1 | 1 | 1 | 1 |
| 15 μl | 5 mg/ml | 2* | 2.5* | 3* | 1 | 1 | 3* |
|  | 4 mg/ml | 1.5* | 2* | 3* | 1 | 1 | 3* |
|  | 3 mg/ml | 1.5* | 2* | 2* | 1 | 1 | 2* |
|  | 2 mg/ml | 1 | 1.5 | 1.5 | 1 | 1 | 1.5 |
|  | 1 mg/ml | 1 | 1 | 1 | 1 | 1 | 1 |
| 20 μl | 5 mg/ml | 2* | 3* | 3* | 1 | 1 | 3* |
|  | 4 mg/ml | 2* | 3* | 3* | 1 | 1 | 3* |
|  | 3 mg/ml | 1.5* | 2* | 3* | 1 | 1 | 2* |
|  | 2 mg/ml | 1 | 1.5 | 1.5 | 1 | 1 | 1.5 |
|  | 1 mg/ml | 1 | 1 | 1 | 1 | 1 | 1 |
| 25 μl | 5 mg/ml | 2* | 3* | 3* | 1 | 1 | 3* |
|  | 4 mg/ml | 2* | 3* | 3* | 1 | 1 | 3* |
|  | 3 mg/ml | 1.5* | 2* | 3* | 1 | 1 | 2* |
|  | 2 mg/ml | 1 | 1.5 | 1.5 | 1 | 1 | 1.5 |
|  | 1 mg/ml | 1 | 1 | 1 | 1 | 1 | 1 |

TABLE 4

Visual assessment of aqueous compositions produced by mixing glucagon/Benzalkonium solution with solutions A-F. Benzalkonium chloride concentration was 0.025% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 5 μl | 5 mg/ml | 1.5 | 1.5* | 1.5* | 1 | 1 | 1.5 |
|  | 4 mg/ml | 1.5 | 1.5* | 1.5* | 1 | 1 | 1.5 |
|  | 3 mg/ml | 1 | 1 | 1.5 | 1 | 1 | 1 |
|  | 2 mg/ml | 1 | 1 | 1.5 | 1 | 1 | 1 |
|  | 1 mg/ml | 1 | 1 | 1 | 1 | 1 | 1 |
| 10 μl | 5 mg/ml | 1.5 | 1.5* | 2* | 1 | 1 | 1.5* |
|  | 4 mg/ml | 1.5 | 2* | 2* | 1 | 1 | 1.5* |
|  | 3 mg/ml | 1.5 | 1.5* | 1.5* | 1 | 1 | 1.5* |
|  | 2 mg/ml | 1 | 1 | 1.5 | 1 | 1 | 1 |
|  | 1 mg/ml | 1 | 1 | 1 | 1 | 1 | 1 |
| 15 μl | 5 mg/ml | 1.5* | 2* | 2* | 1 | 1 | 2* |
|  | 4 mg/ml | 1.5* | 2* | 2.5* | 1 | 1 | 2* |
|  | 3 mg/ml | 1.5* | 1.5* | 2* | 1 | 1 | 1.5* |
|  | 2 mg/ml | 1 | 1 | 1.5 | 1 | 1 | 1.5* |
|  | 1 mg/ml | 1 | 1 | 1 | 1 | 1 | 1 |
| 20 μl | 5 mg/ml | 2* | 2.5* | 3* | 1 | 1 | 2.5* |
|  | 4 mg/ml | 2* | 2.5* | 3* | 1 | 1 | 2.5* |
|  | 3 mg/ml | 1.5* | 1.5* | 2* | 1 | 1 | 1.5* |
|  | 2 mg/ml | 1.5 | 1.5 | 1.5 | 1 | 1 | 1.5* |
|  | 1 mg/ml | 1 | 1 | 1.5 | 1 | 1 | 1.5 |
| 25 μl | 5 mg/ml | 2.5* | 3* | 3* | 1 | 1.5 | 2.5* |
|  | 4 mg/ml | 2* | 2.5* | 3* | 1 | 1 | 2.5* |
|  | 3 mg/ml | 1.5* | 1.5* | 2* | 1 | 1 | 1.5* |
|  | 2 mg/ml | 1.5 | 1.5 | 2 | 1 | 1 | 1.5* |
|  | 1 mg/ml | 1 | 1 | 1.5 | 1 | 1 | 1.5 |

TABLE 5

Visual assessment of aqueous compositions produced by mixing glucagon/Benzethonium solution with solutions A-F. Benzethonium chloride concentration was 0.01% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 5 μl | 5 mg/ml | 1* | 1.5* | 1.5* | 1 | 1 | 1.5* |
|  | 4 mg/ml | 1* | 1.5* | 1.5* | 1 | 1 | 1 |
|  | 3 mg/ml | 1 | 1 | 1 | 1 | 1 | 1 |
|  | 2 mg/ml | 1 | 1 | 1 | 1 | 1 | 1 |
|  | 1 mg/ml | 1 | 1 | 1 | 1 | 1 | 1 |
| 10 μl | 5 mg/ml | 1.5* | 1.5* | 1.5* | 1 | 1 | 1.5* |
|  | 4 mg/ml | 1.5* | 1.5* | 1.5* | 1 | 1 | 1.5* |
|  | 3 mg/ml | 1.5* | 1.5* | 1.5* | 1 | 1 | 1.5* |
|  | 2 mg/ml | 1.5 | 1.5 | 1.5 | 1 | 1 | 1 |
|  | 1 mg/ml | 1 | 1 | 1 | 1 | 1 | 1 |
| 15 μl | 5 mg/ml | 2* | 2* | 2* | 1 | 1 | 2* |
|  | 4 mg/ml | 1.5* | 2* | 2* | 1 | 1 | 2* |
|  | 3 mg/ml | 1.5* | 1.5* | 1.5* | 1 | 1 | 1.5* |
|  | 2 mg/ml | 1.5 | 1.5 | 1.5 | 1 | 1 | 1.5* |
|  | 1 mg/ml | 1 | 1 | 1 | 1 | 1 | 1 |
| 20 μl | 5 mg/ml | 2* | 2* | 2* | 1 | 1.5* | 2* |
|  | 4 mg/ml | 2* | 2* | 2* | 1 | 1.5* | 2* |
|  | 3 mg/ml | 1.5* | 1.5* | 2* | 1 | 1.5* | 1.5* |
|  | 2 mg/ml | 1.5* | 1.5* | 1.5* | 1 | 1 | 1.5 |
|  | 1 mg/ml | 1 | 1 | 1 | 1 | 1 | 1 |
| 25 μl | 5 mg/ml | 2* | 2.5* | 2.5* | 1 | 1.5* | 2.5* |
|  | 4 mg/ml | 2* | 2* | 2* | 1 | 1.5* | 2* |
|  | 3 mg/ml | 1.5* | 1.5* | 2* | 1 | 1.5 | 1.5* |
|  | 2 mg/ml | 1.5* | 1.5* | 1.5* | 1 | 1 | 1.5 |
|  | 1 mg/ml | 1 | 1 | 1 | 1 | 1 | 1 |

TABLE 6

Visual assessment of aqueous compositions produced by mixing glucagon/Benzalkonium solution with solutions A-F. Benzalkonium chloride concentration was 0.01% (w/v). Extent of visible precipitation graded on a scale 1-3; 1 = clear solution; 3 = significant precipitation; *= gel formation.

| Volume added | Glucagon | A | B | C | D | E | F |
|---|---|---|---|---|---|---|---|
| 5 μl | 5 mg/ml | 1.5* | 1.5* | 1.5* | 1 | 1 | 1.5* |
|  | 4 mg/ml | 1.5 | 1.5* | 1.5* | 1 | 1 | 1.5 |
|  | 3 mg/ml | 1.5 | 1.5 | 1.5* | 1 | 1 | 1.5 |
|  | 2 mg/ml | 1 | 1 | 1.5 | 1 | 1 | 1 |
|  | 1 mg/ml | 1 | 1 | 1 | 1 | 1 | 1 |
| 10 μl | 5 mg/ml | 2* | 2* | 2* | 1 | 1 | 1.5* |
|  | 4 mg/ml | 1.5* | 2* | 2* | 1 | 1 | 1.5* |
|  | 3 mg/ml | 1.5 | 1.5* | 1.5* | 1 | 1 | 1.5* |
|  | 2 mg/ml | 1.5 | 1.5 | 1.5 | 1 | 1 | 1.5 |
|  | 1 mg/ml | 1.5 | 1.5 | 1.5 | 1 | 1 | 1.5 |
| 15 μl | 5 mg/ml | 2* | 2.5* | 2.5* | 1 | 1.5 | 2* |
|  | 4 mg/ml | 2* | 2* | 2.5* | 1 | 1 | 2* |
|  | 3 mg/ml | 1.5 | 1.5* | 2* | 1 | 1 | 2* |
|  | 2 mg/ml | 1.5 | 1.5 | 1.5 | 1 | 1 | 1.5 |
|  | 1 mg/ml | 1.5 | 1.5 | 1.5 | 1 | 1 | 1.5 |
| 20 μl | 5 mg/ml | 2* | 2.5* | 2.5* | 1 | 1.5 | 2* |
|  | 4 mg/ml | 2* | 2* | 2.5* | 1 | 1 | 2* |
|  | 3 mg/ml | 1.5 | 1.5* | 2* | 1 | 1 | 2* |
|  | 2 mg/ml | 1.5 | 1.5 | 1.5 | 1 | 1 | 1.5 |
|  | 1 mg/ml | 1.5 | 1.5 | 1.5 | 1 | 1 | 1.5 |
| 25 μl | 5 mg/ml | 2.5* | 2.5* | 3* | 1 | 1.5 | 2.5* |
|  | 4 mg/ml | 2* | 2.5* | 3* | 1 | 1 | 2.5* |
|  | 3 mg/ml | 1.5 | 2* | 2.5* | 1 | 1 | 2.5 |
|  | 2 mg/ml | 1.5 | 1.5 | 2 | 1 | 1 | 2 |
|  | 1 mg/ml | 1.5 | 1.5 | 1.5 | 1 | 1 | 1.5 |

TABLE 7

Visual assessment of aqueous compositions produced by mixing glucagon/
Benzethonium solution with solutions A-F. Benzethonium chloride
concentration was 0.005% (w/v). Extent of visible precipitation graded
on a scale 1-3; 1 = 0 clear solution; 3 = significant precipitation;
*= gel formation.

| Volume added | Glucagon | A | B | C | D | E | F |
|---|---|---|---|---|---|---|---|
| 5 µl | 5 mg/ml | 1.5* | 1.5* | 1.5* | 1 | 1 | 1 |
| | 4 mg/ml | 1.5* | 1.5* | 1.5* | 1 | 1 | 1 |
| | 3 mg/ml | 1.5 | 1.5 | 1.5 | 1 | 1 | 1 |
| | 2 mg/ml | 1 | 1 | 1 | 1 | 1 | 1 |
| | 1 mg/ml | 1 | 1 | 1 | 1 | 1 | 1 |
| 10 µl | 5 mg/ml | 1.5* | 1.5* | 1.5* | 1 | 1 | 1.5* |
| | 4 mg/ml | 1.5* | 1.5* | 1.5* | 1 | 1 | 1.5* |
| | 3 mg/ml | 1.5* | 1.5* | 1.5* | 1 | 1 | 1.5* |
| | 2 mg/ml | 1.5* | 1.5* | 1.5* | 1 | 1 | 1.5 |
| | 1 mg/ml | 1 | 1 | 1 | 1 | 1 | 1 |
| 15 µl | 5 mg/ml | 1.5* | 2* | 2* | 1 | 1.5* | 2* |
| | 4 mg/ml | 1.5* | 2* | 2* | 1 | 1.5* | 2* |
| | 3 mg/ml | 1.5* | 1.5* | 1.5* | 1 | 1 | 1.5* |
| | 2 mg/ml | 1.5* | 1.5* | 1.5* | 1 | 1 | 1.5 |
| | 1 mg/ml | 1 | 1 | 1 | 1 | 1 | 1 |
| 20 µl | 5 mg/ml | 1.5* | 2* | 2* | 1 | 1.5* | 2* |
| | 4 mg/ml | 1.5* | 2* | 2* | 1 | 1.5* | 2* |
| | 3 mg/ml | 1.5* | 1.5* | 1.5* | 1 | 1.5* | 1.5* |
| | 2 mg/ml | 1.5 | 1.5 | 1.5 | 1 | 1 | 1.5 |
| | 1 mg/ml | 1 | 1 | 1 | 1 | 1 | 1 |
| 25 µl | 5 mg/ml | 2* | 2* | 2* | 1 | 1.5* | 2* |
| | 4 mg/ml | 1.5* | 2* | 2* | 1 | 1.5* | 2* |
| | 3 mg/ml | 1.5* | 1.5* | 1.5* | 1 | 1.5* | 1.5* |
| | 2 mg/ml | 1.5 | 1.5 | 1.5 | 1 | 1 | 1.5 |
| | 1 mg/ml | 1 | 1 | 1 | 1 | 1 | 1 |

TABLE 8

Visual assessment of aqueous compositions produced by mixing glucagon/
Benzalkonium solution with solutions A-F. Benzalkonium chloride
concentration was 0.005% (w/v). Extent of visible precipitation graded
on a scale 1-3; 1 = clear solution; 3 = significant precipitation;
*= gel formation.

| Volume added | Glucagon | A | B | C | D | E | F |
|---|---|---|---|---|---|---|---|
| 5 µl | 5 mg/ml | 1.5* | 1.5* | 2* | 1 | 1 | 1.5* |
| | 4 mg/ml | 1.5 | 1.5* | 1.5* | 1 | 1 | 1.5 |
| | 3 mg/ml | 1 | 1.5 | 1.5* | 1 | 1 | 1 |
| | 2 mg/ml | 1 | 1 | 1 | 1 | 1 | 1 |
| | 1 mg/ml | 1 | 1 | 1 | 1 | 1 | 1 |
| 10 µl | 5 mg/ml | 1.5* | 1.5* | 2* | 1 | 1 | 1.5* |
| | 4 mg/ml | 1.5* | 1.5* | 1.5* | 1 | 1 | 1.5* |
| | 3 mg/ml | 1 | 1.5* | 1.5* | 1 | 1 | 1.5 |
| | 2 mg/ml | 1 | 1 | 1.5 | 1 | 1 | 1.5 |
| | 1 mg/ml | 1 | 1 | 1 | 1 | 1 | 1 |
| 15 µl | 5 mg/ml | 2* | 2* | 2.5* | 1 | 1 | 2* |
| | 4 mg/ml | 1.5* | 2* | 2* | 1 | 1 | 2* |
| | 3 mg/ml | 1.5 | 1.5* | 1.5* | 1 | 1 | 1.5 |
| | 2 mg/ml | 1 | 1.5 | 1.5 | 1 | 1 | 1.5 |
| | 1 mg/ml | 1 | 1 | 1 | 1 | 1 | 1 |
| 20 µl | 5 mg/ml | 2* | 2.5* | 3* | 1 | 1.5 | 2.5* |
| | 4 mg/ml | 1.5* | 2* | 2.5* | 1 | 1.5 | 2* |
| | 3 mg/ml | 1.5 | 2* | 2* | 1 | 1 | 1.5 |
| | 2 mg/ml | 1 | 1.5 | 1.5 | 1 | 1 | 1.5 |
| | 1 mg/ml | 1 | 1 | 1.5 | 1 | 1 | 1 |
| 25 µl | 5 mg/ml | 2* | 2.5* | 3* | 1 | 1.5 | 3* |
| | 4 mg/ml | 1.5* | 2* | 2.5* | 1 | 1.5 | 2.5* |
| | 3 mg/ml | 1.5 | 2* | 2.5* | 1 | 1 | 2 |
| | 2 mg/ml | 1 | 1.5 | 1.5 | 1 | 1 | 1.5 |
| | 1 mg/ml | 1 | 1 | 1.5 | 1 | 1 | 1 |

Conclusion from the Experiments Described in Tables 3-8:

Tables 3-8 show the results of the same type of experiment as that described in Tables 1 and 2, using different initial concentration of the cationic surfactant. The conclusions that can be drawn from these additional results are aligned with those made above from Tables 1 and 2 i.e., the solubility of glucagon being dependent on pH and ionic strength in the presence of all cationic surfactants tested. The pH 6 and particularly pH 4 generally slightly acidic pH) is preferable to pH 7.4 (i.e., approximately neutral pH). In addition, using an uncharged tonicity modifier (such as 1,2-propanediol) is preferable to using a charged tonicity modifier (such as NaCl), especially at higher glucagon concentrations. Reducing the concentration of the cationic surfactant results in decreased solubility of glucagon (e.g., compare Table 1 and Table 7 to see extremes of benzethonium concentration). However, even using the lowest benzethonium and benzalkonium concentrations (0.005% w/v), it is possible to produce clear, approximately isotonic, solutions of glucagon at the pH values tested <7.4 even at high concentration when the composition employs an uncharged rather than a charged tonicity modifier (see Tables 10 and 11).

The Figures show the results of turbidity measurements. The general conclusions are in line with those drawn from the visual assessment of the compositions (Tables 1-8).

From FIG. 1 if may be concluded that using lower pH (4 and 6) and uncharged tonicity modifier allows better solubility of glucagon in the presence of 0.05% w/v Benzethonium chloride than formulations at higher pH (7.4) and formulations containing sodium chloride as tonicity modifier.

Figure 2:
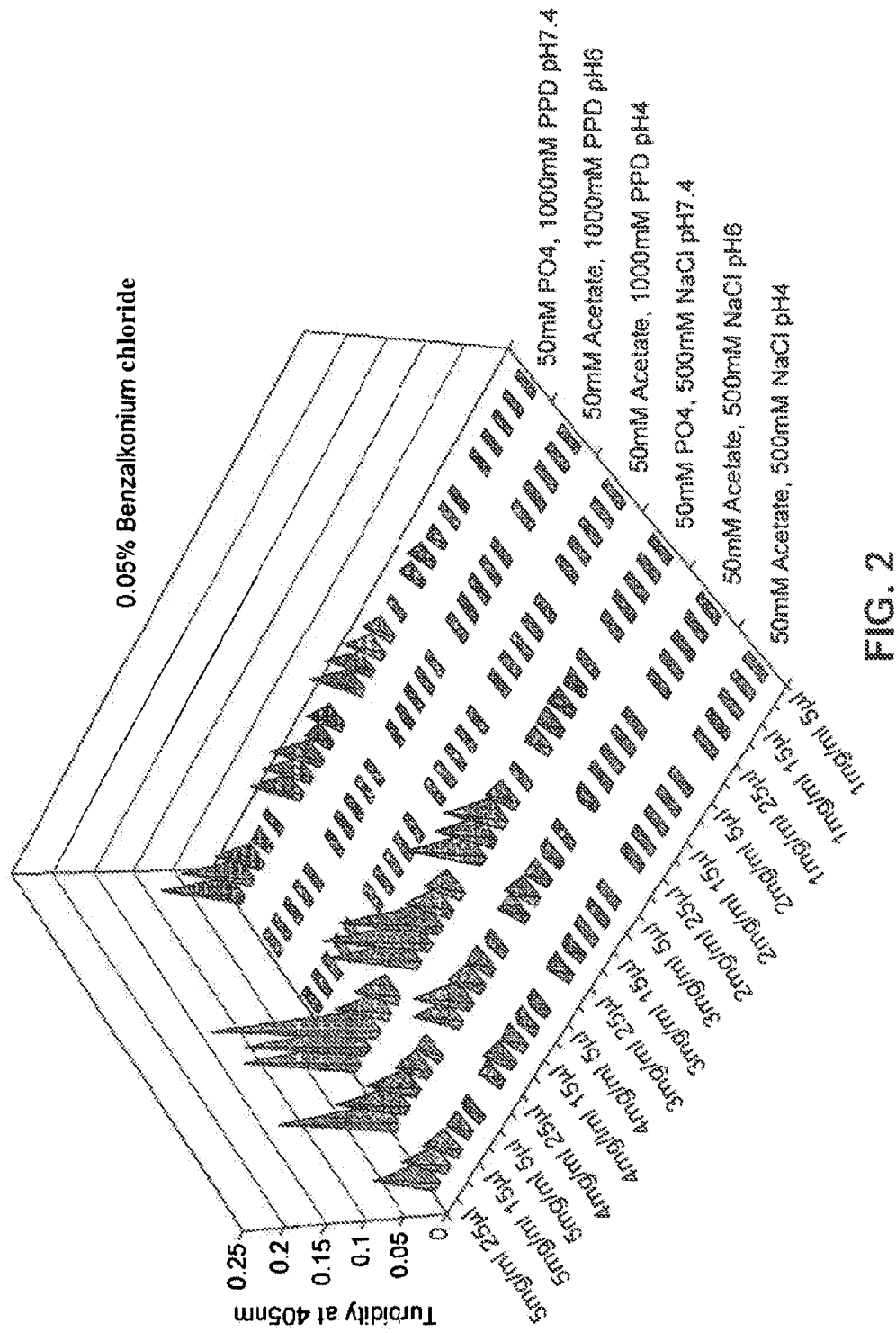
FIG. 2. Turbidity (405 nm) of aqueous compositions produced by mixing glucagon/Benzalkonium solution with solutions A-F ((A) 50 mM acetate+500 mM NaCl (pH 4), (B) 50 mM acetate+500 mM NaCl (pH 6), (C) 50 mM phosphate+500 mM NaCl (pH 7.4), (D) 50 mM acetate+1000 mM 1,2-propanediol (pH 4), (E) 50 mM acetate+1000 mM 1,2-propanediol (pH 6.6), and (F) 50 mM phosphate+1000 mM 1,2-propanediol (pH 7.4)). Benzalkonium chloride concentration was 0.05% (w/v).

From FIG. 2 it may be concluded, that using lower pH (4 and 6) and uncharged tonicity modifier allows better solubility of glucagon in the presence of 0.05% w/v Benzalkonium chloride than formulations at higher pH (7.4) and formulations containing sodium chloride as tonicity modifier.

Figure 3:
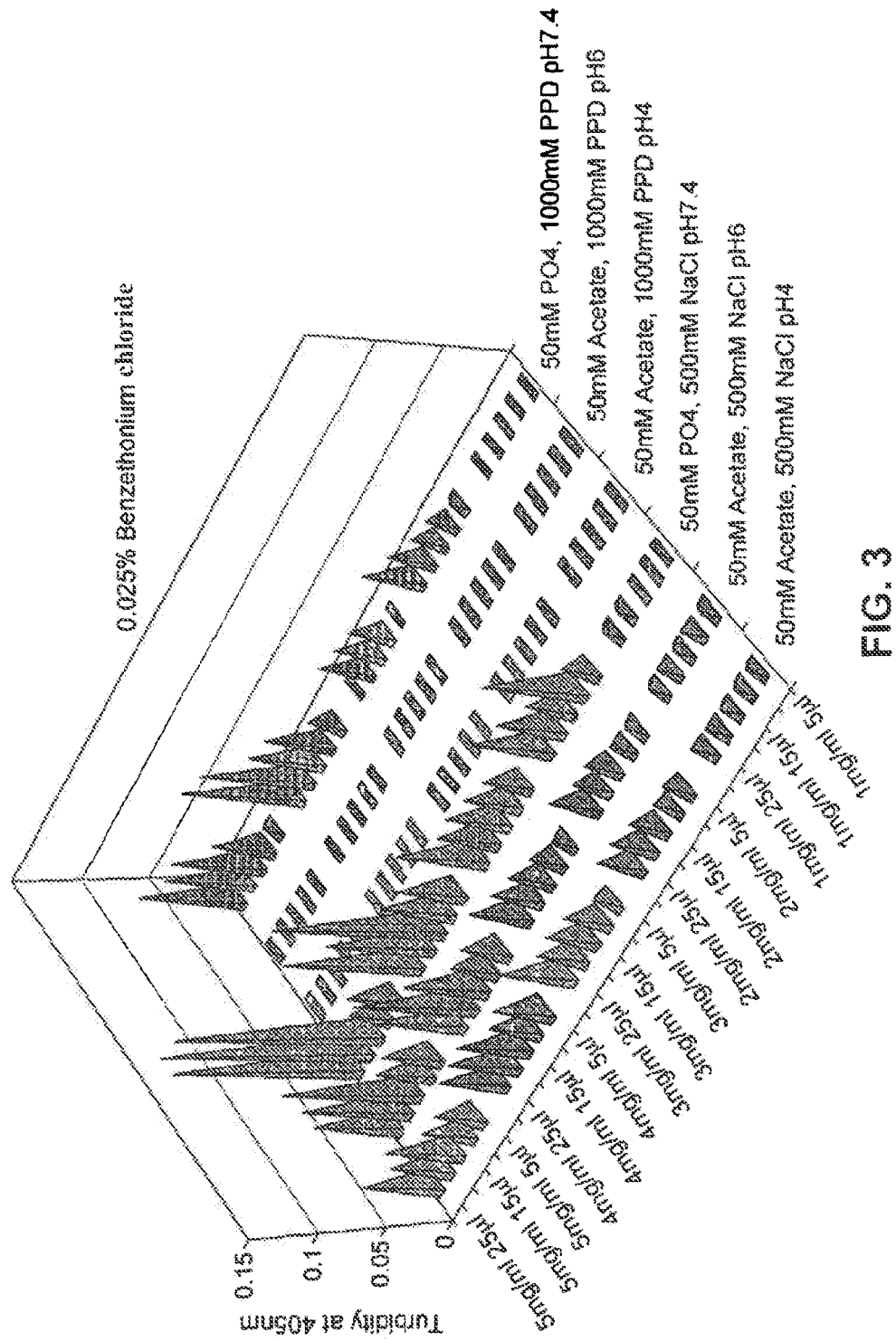
FIG. 3. Turbidity (405 nm) of aqueous compositions produced by mixing glucagon/Benzethonium solution with solutions A-F ((A) 50 mM acetate+500 mM NaCl (pH 4, (B) 50 mM acetate+500 mM NaCl (pH 6), (C) 500 mM phosphate+500 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+1000 mM 1,2-propanediol (pH 7.4)). Benzethonium chloride concentration was 0.025% (w/v).

From FIG. 3 it may be concluded that using lower pH (4 and 6) and uncharged tonicity modifier allows better solubility of glucagon in the presence of 0.025% w/v Benzethonium chloride than formulations at higher pH (7.4) and formulations containing sodium chloride as tonicity modifier.

Figure 4:
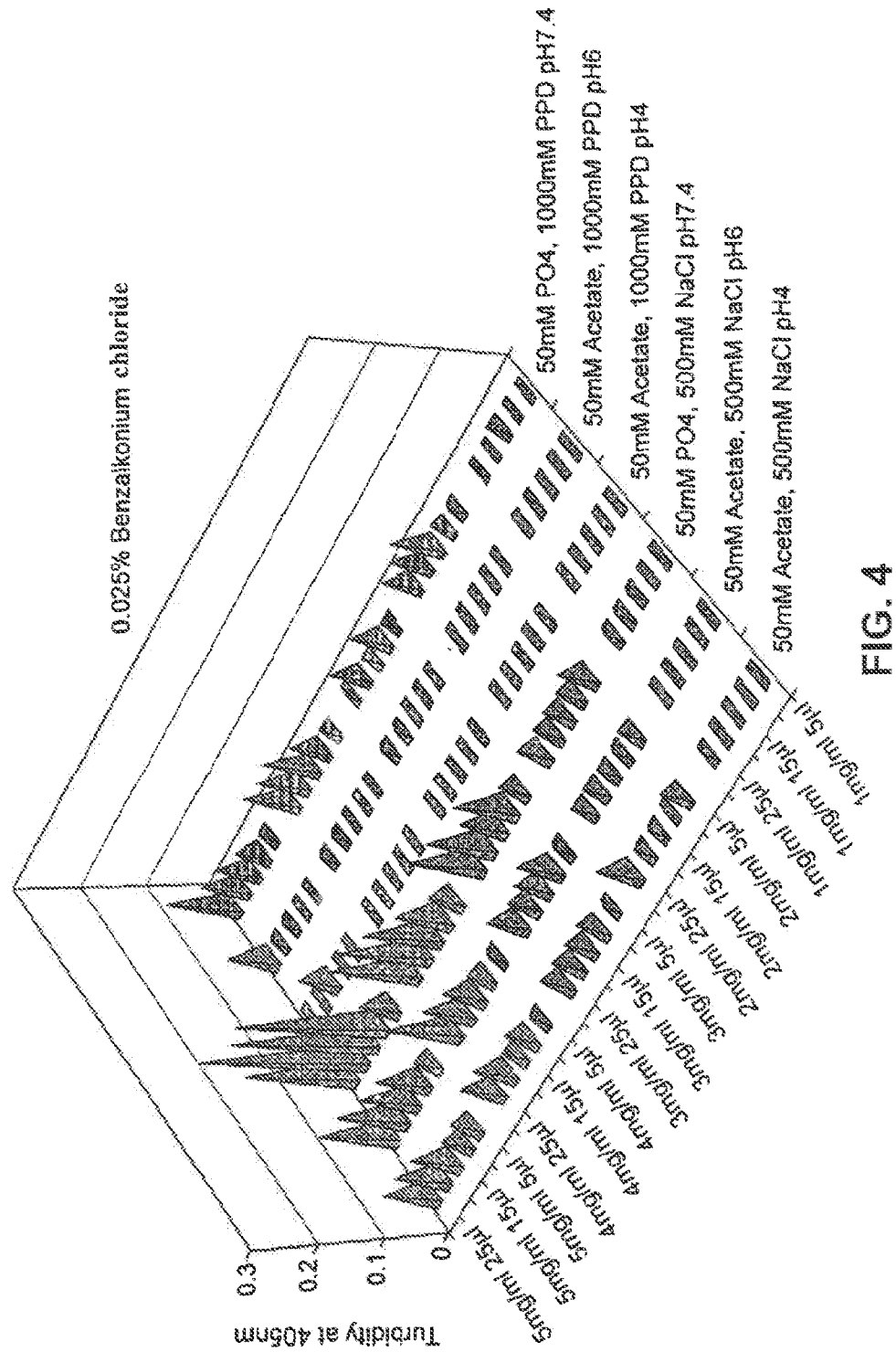
FIG. 4. Turbidity (405 nm) of aqueous compositions produced by mixing glucagon/Benzalkonium solution with solutions A-F ((A) 50 mM acetate+509 mM NaCl (pH 4), (B) 50 mM acetate+500 mM NaCl (pH 6), (C) 50 mM phosphate+5.00 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+1000 mM 1,2-propanediol (pH 7.4)). Benzalkonium chloride concentration was 0.025% (w/v).

From FIG. 4 it may be concluded that using lower pH (4 and 6) and uncharged tonicity modifier allows better solubility of glucagon in the presence of 0.025% w/v Benzalkonium chloride than formulations at higher pH (7.4) and formulations containing sodium chloride as tonicity modifier.

Figure 5:
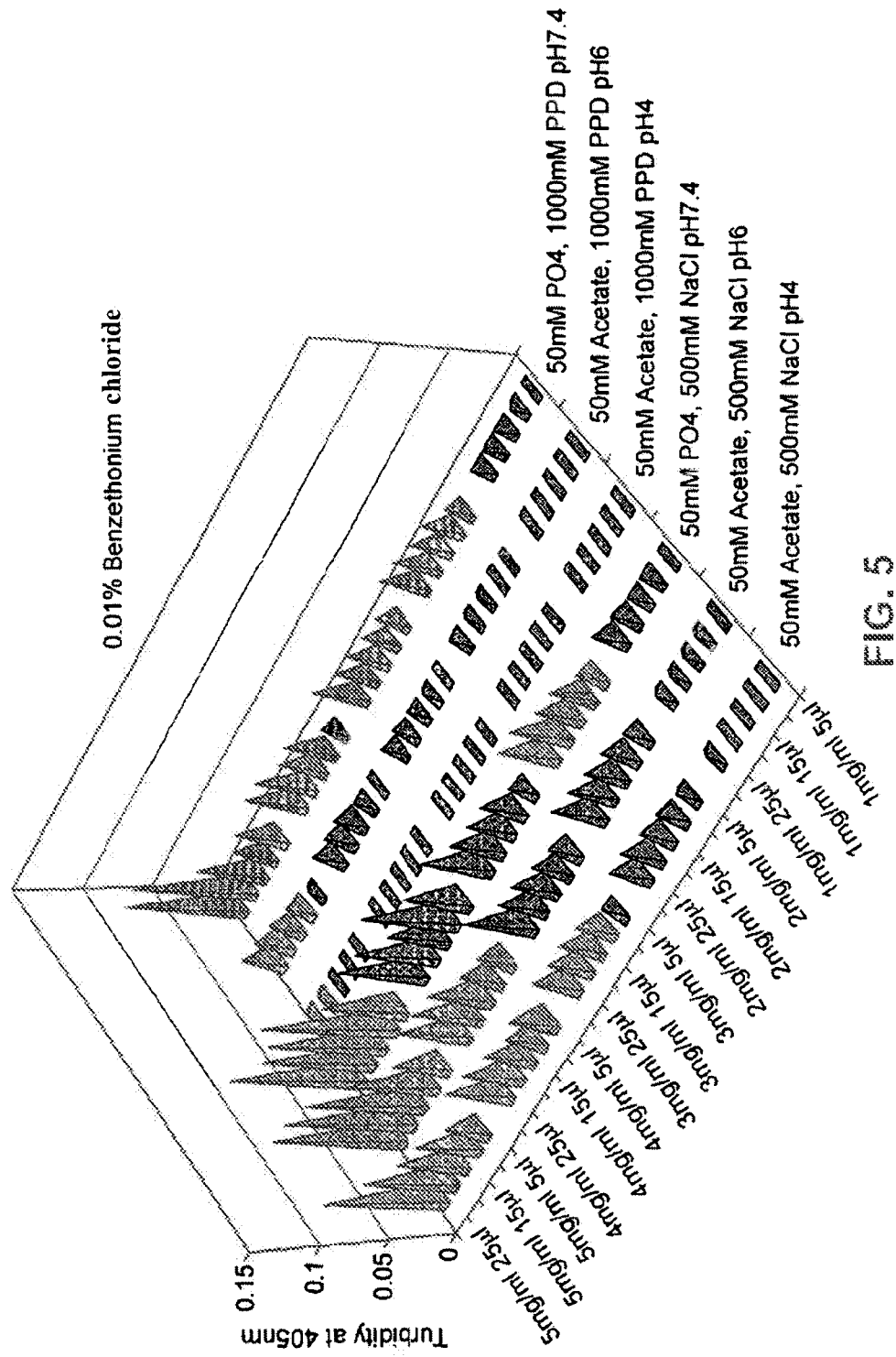
FIG. 5. Turbidity (405 nm) of aqueous compositions produced by mixing glucagon/Benzethonium solution with solutions A-F ((A) 50 mM acetate+500 mM NaCl (pH 4), (B) 50 mM acetate+500 mM NaCl (pH 6), (C) 50 mM phosphate+500 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+1000 mM 1,2-propanediol (pH 7.4)). Benzalkonium chloride concentration was 0.01% (w/v).

From FIG. 5 it may be concluded that using lower pH (4 and 6, and especially 4) and uncharged tonicity modifier allows better solubility of glucagon in the presence of 0.01% w/v Benzethonium chloride than formulations at higher pH (7.4) and formulations containing sodium chloride as tonicity modifier.

Figure 6:
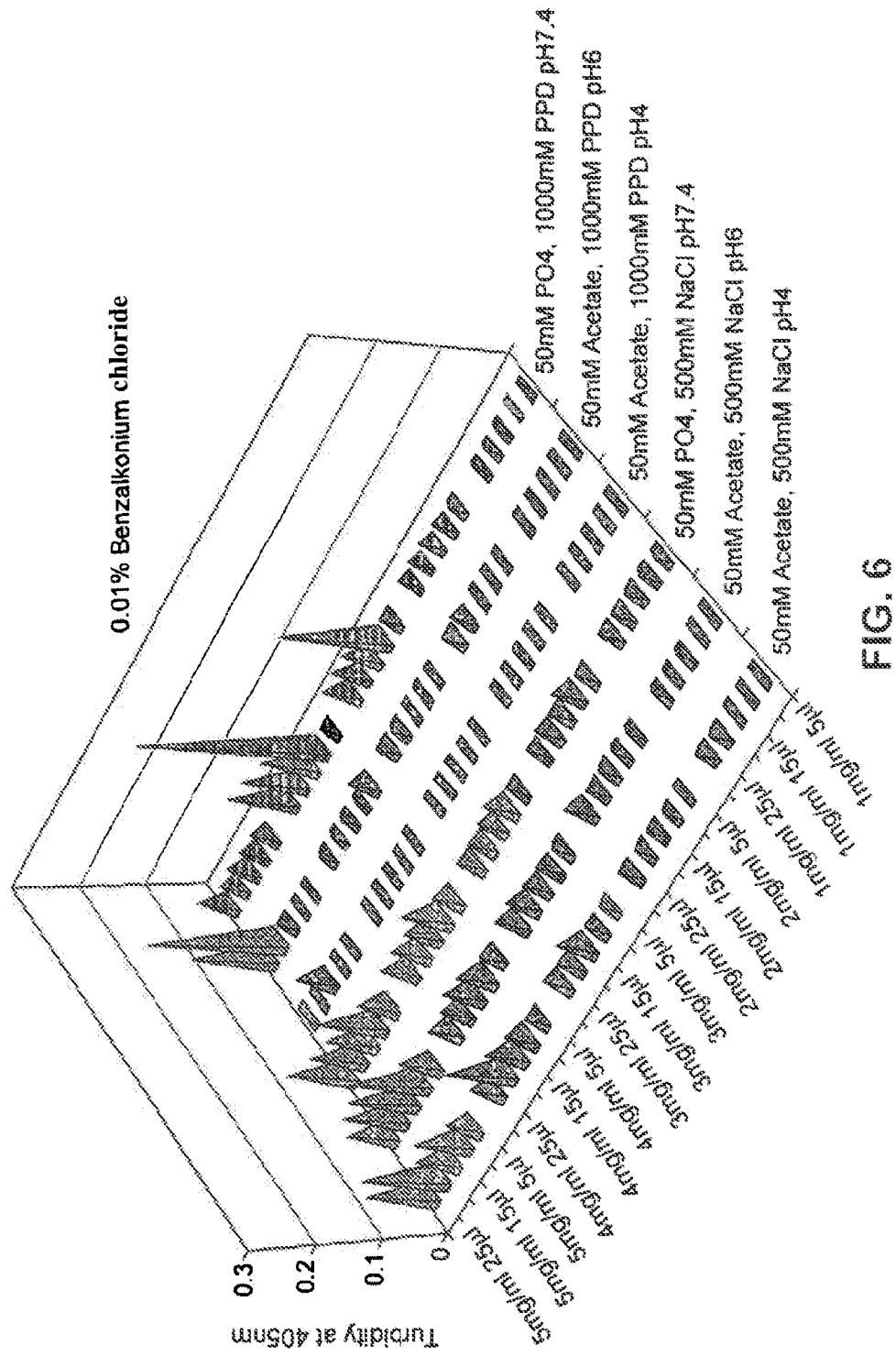
FIG. 6. Turbidity (405 nm) of aqueous compositions produced by mixing glucagon/Benzalkonium solution with solutions A-F ((A) 50 mM acetate+500 mM NaCl (pH 4), (B) 50 mM acetate+500 mM NaCl (pH 6), (C) mM phosphate+500 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+1000 mM 1,2-propanediol (pH 7.4)). Benzalkonium chloride concentration was 0.01% (w/v).

From FIG. 6 it may be concluded that using lower pH (4 and 6) and uncharged tonicity modifier allows better solubility of glucagon in the presence of 0.01% w/v Benzalkonium chloride than formulations at higher pH (7.4) and formulations containing sodium chloride as tonicity modifier.

Figure 7:
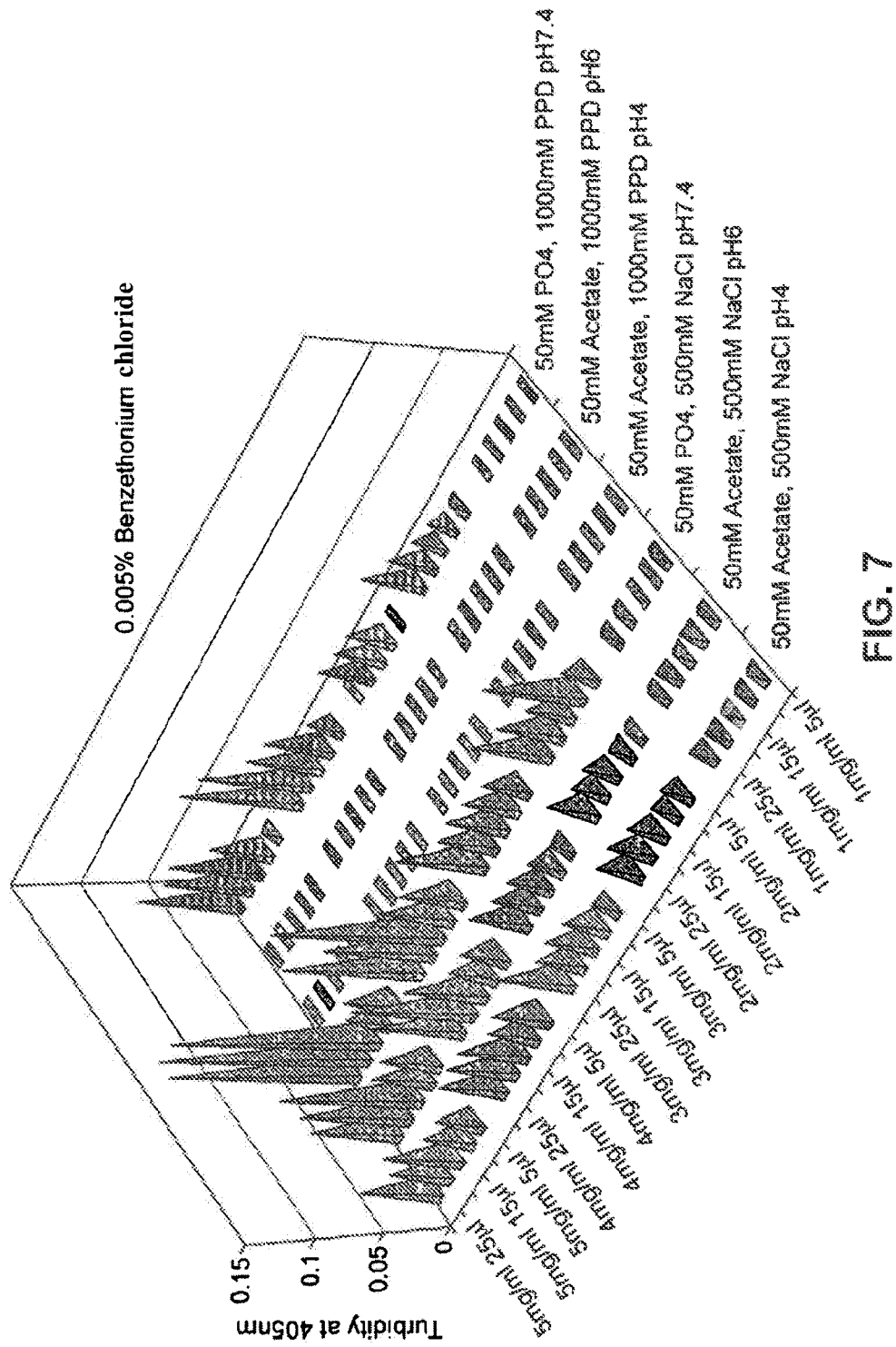
FIG. 7. Turbidity (405 nm) of aqueous compositions produced by mixing glucagon/Benzethonium solution with solutions A-F ((A) 50 mM acetate+500 mM NaCl (pH 4), (B) 50 mM acetate+500 mM NaCl (pH 6), (C) 50 mM phosphate+500 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+10 mM 1,2-propanediol (pH 7.4)). Benzethonium chloride concentration was 0.005% (w/v).

From FIG. 7 it may be concluded that using lower pH (4 and 6) and uncharged tonicity modifier allows better solubility of glucagon in the presence of 0.005% w/v Benzethonium chloride than formulations at higher pH (7.4) and formulations containing sodium chloride as tonicity modifier. Even at such low concentration of Benzethonium chloride, clear, non-viscous and approximately isotonic compositions of glucagon can be prepared under the optimal pH and ionic strength (i.e., slightly acidic pH and low ionic strength).

Figure 8:
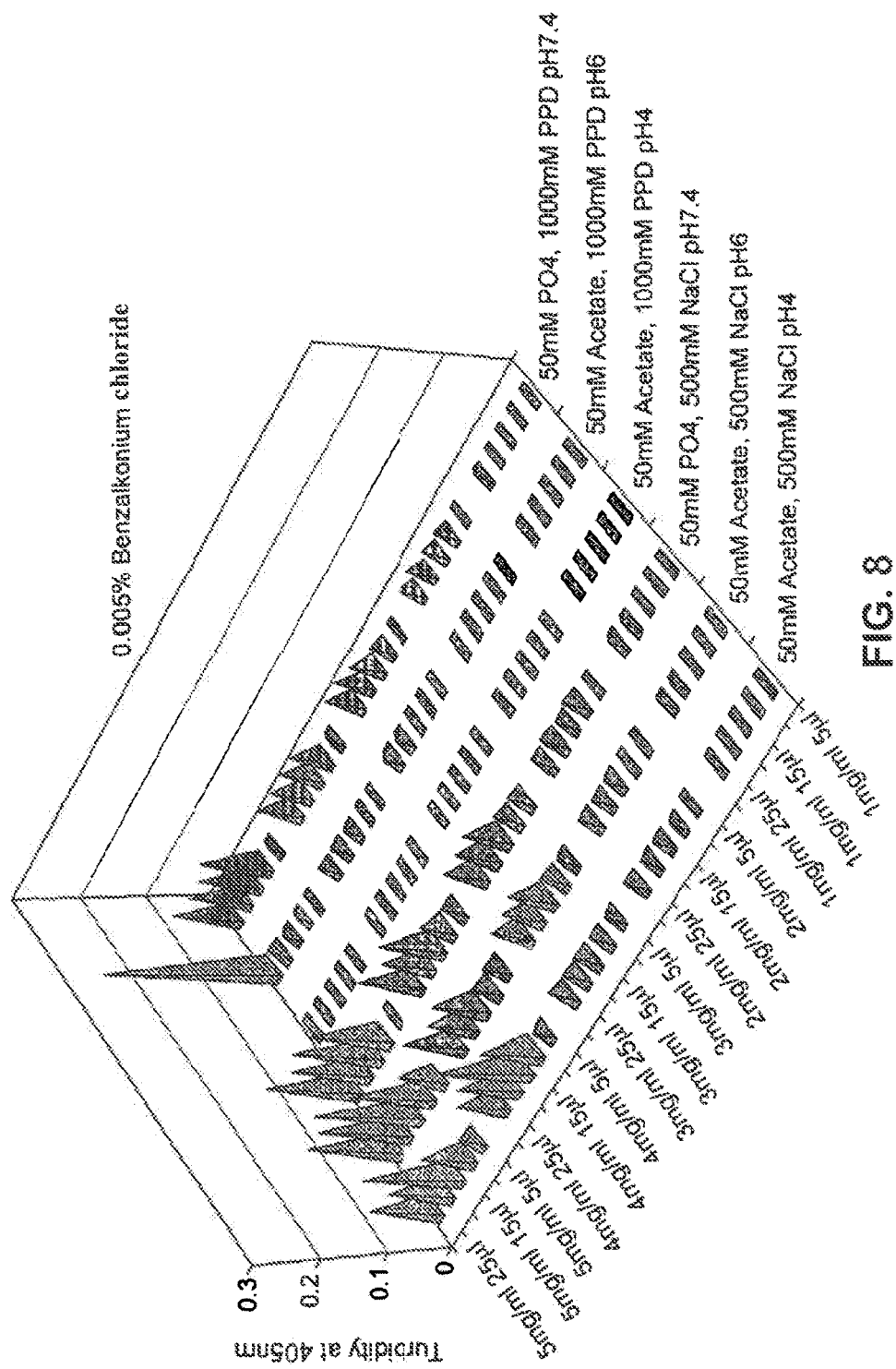
FIG. 8. Turbidity (405 nm) of aqueous compositions produced by mixing glucagon/Benzalkonium solution with solutions A-F ((A) 50 mM acetate+500 mM NaCl (pH 4), (B) 50 mM acetate+500 mM NaCl (pH 6), (C) 50 mM phosphate+500 mM NaCl (pH 7.4), (D) 50 mM acetate+1000 mM 1,2-propanediol (pH 4), (E) 50 mM acetate+1000 mM 1,2-propanediol (pH 6), and (F) 50 mM phosphate+1000 mM 1,2-propanediol (pH 7.4)). Benzalkonium chloride concentration was 0.005% (w/v).

From FIG. 8 it may be concluded that using lower pH (4 and 6) and uncharged tonicity modifier allows better solubility of glucagon in the presence of 0.005% w/v Benzalkonium chloride than formulations at higher pH (7.4) and formulations containing sodium chloride as tonicity modifier. Even at this concentration of Benzalkonium chloride, clear, non-viscous and approximately isotonic compositions of glucagon can be prepared under the optimal pH and ionic strength (i.e., slightly acidic pH and low ionic strength).

Summary of Results

It was demonstrated that the solubility of glucagon in the presence of cationic surfactants benzalkonium chloride and benzethonium chloride is dependent on pH. Another consideration is the presence of charged species. The solubility is considerably higher at pH 4-6 than at pH 7.4 at all concentrations of the cationic surfactants tested (0.005%-0.05% w/v). This conclusion can be made from all Tables (1-8) and all FIGS. (1-8) by comparing the compositions at pH 7.4 versus those at pH 4 and 6. In addition, the solubility of glucagon is compromised in the presence of charged species, this effect being especially noticeable at higher concentrations of glucagon. This conclusion can be made from all Tables (1-8) and all FIGS. (1-8) by comparing the compositions containing 1,2-propanediol as the key tonicity modifier versus those relying on NaCl as the key tonicity modifier.

Example 3

Further Investigation of the Effect of Surfactants on the Solubility of Glucagon Purpose of the Experiment Glucagon solubility in aqueous solutions between pH 3 to 9 is extremely low. The purpose of this experiment was to assess the effect of the concentration of the surfactants benzethonium chloride and benzalkonium chloride, on the solubility of glucagon at pH 4.5 and pH 5.5, by means of visual assessment upon preparation and after storage. Base formulations were used that included a single buffer (5 mM acetate) and tonicity modifier (250 mM mannitol), at either pH 4.5 or pH 5.5. The surfactant excipients were tested at a range of selected concentrations as indicated.

Experimental Procedure

Approximately 2 mg of glucagon was weighed out into a glass vial and the solution of excipients in one of the base formulations was added to give final glucagon concentration of 1 mg/ml. The concentration of surfactant used ranged from 0.01% to 0.6% w/v specifically 0.01, 0.025, 0.05, 0.075, 0.1, 0.15, 0.2, 0.4 and 0.6% w/v. Visual observations were made at time zero and 14 weeks.

Results

The Tables which are presented below show the formulations prepared and the results of visual assessments:

TABLE 9

Extent of visible precipitation graded on a scale 1-3;
1 = clear solution; 3 = significant precipitation; *= gel formation.

| Mannitol (mM) | Acetate (mM) | Benzethonium chloride % w/v | pH | Time zero | Fourteen weeks 4° C. | Fourteen weeks 40° C. |
|---|---|---|---|---|---|---|
| 250 | 5 | 0.01 | 4.5 | 1 | 2* | 1* |
| 250 | 5 | 0.01 | 5.5 | 1 | 1* | 1* |
| 250 | 5 | 0.025 | 4.5 | 1 | 1* | 1* |
| 250 | 5 | 0.025 | 5.5 | 1 | 3 | 1* |
| 250 | 5 | 0.05 | 4.5 | 1 | 3 | 3 |
| 250 | 5 | 0.05 | 5.5 | 1 | 3 | 3 |
| 250 | 5 | 0.075 | 4.5 | 1 | 3 | 3 |
| 250 | 5 | 0.075 | 5.5 | 1 | 3 | 3 |
| 250 | 5 | 0.1 | 4.5 | 1 | 3 | 3 |
| 250 | 5 | 0.1 | 5.5 | 1 | 2 | 2 |
| 250 | 5 | 0.15 | 4.5 | 1 | 1 | 1 |
| 250 | 5 | 0.15 | 5.5 | 1 | 1 | 1 |
| 250 | 5 | 0.2 | 4.5 | 1 | 1 | 1 |
| 250 | 5 | 0.2 | 5.5 | 1 | 1 | 1 |
| 250 | 5 | 0.4 | 4.5 | 1 | 1 | 1 |
| 250 | 5 | 0.4 | 5.5 | 1 | 1 | 1 |
| 250 | 5 | 0.6 | 4.5 | 1 | 1 | 1 |
| 250 | 5 | 0.6 | 5.5 | 1 | 1 | 1 |

Conclusion from the Experiment Described in Table 9:

The visual observations shown in Table 9 indicate that clear aqueous solutions are formed upon preparation of all formulations. After storage for 14 weeks at 40° C., preparations containing benzethonium chloride in the concentration range 0.15-0.6% w/v remain as clear aqueous solutions. Concentrations at the lower end of this range (e.g., 0.15-02% w/v) are likely to be preferred for biocompatibility reasons. Dependent upon pH 0.01-0.025% w/v benzethonium chloride can also provide useful preparations in the form of clear aqueous gels.

TABLE 10

Extent of visible precipitation graded on a scale 1-3;
1 = clear solution; 3 = significant precipitation; *= gel formation.

| mannitol (mM) | Acetate (mM) | Benzalkonium chloride % w/v | pH | Time zero | Fourteen weeks 4° C. | Fourteen weeks 40° C. |
|---|---|---|---|---|---|---|
| 250 | 5 | 0.01 | 4.5 | 1 | 1* | 2* |
| 250 | 5 | 0.01 | 5.5 | 1 | 1* | 1* |
| 250 | 5 | 0.025 | 4.5 | 1 | 1* | 2* |
| 250 | 5 | 0.025 | 5.5 | 1 | 1* | 1* |
| 250 | 5 | 0.05 | 4.5 | 1 | 2 | 1* |
| 250 | 5 | 0.05 | 5.5 | 1 | 2 | 1* |
| 250 | 5 | 0.075 | 4.5 | 1 | 2 | 1* |
| 250 | 5 | 0.075 | 5.5 | 1 | 2 | 2 |
| 250 | 5 | 0.1 | 4.5 | 1 | 1 | 1 |
| 250 | 5 | 0.1 | 5.5 | 1 | 1 | 1 |
| 250 | 5 | 0.15 | 4.5 | 1 | 1 | 1 |
| 250 | 5 | 0.15 | 5.5 | 1 | 1 | 1 |
| 250 | 5 | 0.2 | 4.5 | 1 | 1 | 1 |
| 250 | 5 | 0.2 | 5.5 | 1 | 1 | 1 |
| 250 | 5 | 0.4 | 4.5 | 1 | 1 | 1 |
| 250 | 5 | 0.4 | 5.5 | 1 | 1 | 1 |
| 250 | 5 | 0.6 | 4.5 | 1 | 1 | 1 |
| 250 | 5 | 0.6 | 5.5 | 1 | 1 | 1 |

Conclusion from the Experiment Described in Table 10:

the visual observations shown in Table 10 indicate that clear aqueous solutions are formed upon preparation of all formulations. After storage for 14 weeks at 40° C., preparations containing benzalkonium chloride in the concentration range 0.1-0.6% w/v remain as clear aqueous solutions. Concentrations at the lower end of this range (e.g., 0.10-0.2% w/v) are likely to be preferred for biocompatibility reasons. Dependent upon pH, 0.01-0.05% w/v benzalkonium chloride can also provide useful preparations in the form of clear aqueous gels.

Example 4

Effect of Benzethonium Chloride Concentration on the Rate of Glucagon Deamidation Purpose the Experiment The purpose of this experiment was to assess the effect of benzethonium chloride concentration on the deamidation of glucagon following incubation at 4 and 40° C. Visual assessment was performed at the same time to allow correlation between the level of gelling and the deamidation.

Experimental Procedure

Liquid formulations of glucagon (1 mg/ml) were prepared and incubated at 4 and 40° C. Deamidation and visual assessment were determined following 4 months incubation at the specified temperatures. Deamidation was determined by reverse phase chromatography both upon preparation and after storage. Base formulations were used comprising buffer (5 mM acetate), tonicity modifier (250 mM mannitol) and a specified concentration of benzethonium chloride, at pH 5.5. The concentration of benzethonium chloride ranged from 0.01% to 0.6% w/v; specifically 0.01, 0.025, 0.05, 0.075, 0.1, 0.15, 0.2, 0.4 and 0.6% w/v. The reverse phase HPLC method used a C18, 4.6×150 mm, 5 μm column, at 45° C., at a flow rate of 1 mL/min, with 30 μL injection volume and detected at 214 nm. Buffer A was; 200 mM K PO4, pH 2.5, in 20% acetonitrile, and buffer B was, B: 60:40 acetonitrile:water at (Time (minutes):Buffer B (%), 0:5, 5:5, 30:45, 32:90, 35:90, 40:5, and 50:5).

Results and Conclusion

The experimental results are shown in Table 11. It was shown that the benzethonium chloride concentration had a strong effect on the physical stability of glucagon (i.e., gel formation and/or precipitation) as well as the rate of deamidation of glucagon. Higher levels of benzethonium (≥0.15% w/v) resulted in maintaining the liquid non-viscous formulation at both temperatures. However, the deamidation rate was relatively thigh at these benzethonium concentrations. With the lowest levels of benzethonium chloride (0.01% and 0.02% w/v) reduced deamidation was observed and at the end of the storage period the formulations had the form of clear aqueous gels. These compositions may be preferred due to the low deamidation rate.

TABLE 11

Visual assessment and % deamidation in aqueous compositions of glucagon following incubation at 4 and 40° C. Extent of visible precipitation graded on a scale 1-3; 1 = clear solution; 3 = significant precipitation; *= gel formation. (all samples were a clear liquid with <1% deamidated variants on preparation)

| [Benzethonium chloride], % (w/v) | % Deamidation | | Visual assessment | |
|---|---|---|---|---|
| | 4° C. (4 months) | 40° C. (4 months) | 4° C. (4 months) | 40° C. (4 months) |
| 0.01 | 1.9 | 6.8 | 1* | 1* |
| 0.025 | 0.4 | 7.7 | 1 | 1* |
| 0.05 | 0.7 | 4.8 | 1 | 2 |
| 0.075 | 0.8 | 9.3 | 1 | 2 |
| 0.1 | 1.7 | 24.4 | 2 | 1 |
| 0.15 | 3.1 | 27.5 | 1 | 1 |
| 0.2 | 5.0 | 30.9 | 1 | 1 |
| 0.4 | 4.9 | 32.5 | 1 | 1 |
| 0.6 | 4.6 | 30.2 | 1 | 1 |

Example 5

Effect of the Nature of the Tonicity Modifier on the Stability of Glucagon

Purpose of the Experiment

The purpose of this experiment was to assess the effect of selected tonicity modifiers on the solubility of glucagon in the presence of benzethonium chloride at pH 5.5, by means of visual assessment upon preparation and after storage.

Experimental Procedure

Liquid formulations of glucagon (1 mg/ml) were prepared, containing a buffer (5 mM acetate), benzethonium chloride (at a specified concentration) and a tonicity modifier (at a specified concentration), at pH 5.5. In some cases, the composition contained a specified concentration of an antioxidant. The effect of the nature and the concentration of the tonicity modifier on the physical stability (i.e., gel formation and/or aggregation) was determined by visual assessment following storage.

Results and Conclusions

In the first experiment, the effects of mannitol and 1,2-propanediol as tonicity modifiers modifiers were compared at 50° C. The background formulation contained 5 mM acetate, and 0.075% benzethonium chloride and was adjusted to pH 5.5. The results are shown in Table 12. It was shown that mannitol is preferable to 1,2-propanediol as a tonicity modifier. The use of 1,2-propanediol resulted in much earlier onset of aggregation and gel formation compared with the use of mannitol. Use of higher concentration of 1,2-propanediol was not found to improve the glucagon stability.

TABLE 12

Visual assessment of aqueous compositions produced of glucagon following incubation at 50° C. Extent of visible precipitation graded on a scale 1-3; 1 = clear solution; 3 = significant precipitation; *= gel formation.

| | Visual assessment (50° C. incubation) | | | | |
|---|---|---|---|---|---|
| Tonicity modifier | 0 days | 1 week | 3 weeks | 7 weeks | 14 weeks |
| Mannitol (250 mM) | 1 | 1 | 1 | 1 | 1 |
| 1,2-propanediol (250 mM) | 1 | 1* | 1* | 1* | 2 |
| 1,2-propanediol (1000 mM) | 1 | 1* | 1* | 1* | 2 |
| 1,2-propanediol (5000 mM) | 1 | 2 | 3 | 3 | 3 |

In another experiment, the effects of mannitol and glycerol as tonicity modifiers were compared at 50° C. The background formulation contained 5 mM acetate, 0.075% benzethonium chloride and 1.3 mM butylated hydroxytoluene and was adjusted to pH 5.5. The results are shown in Table 13. It was shown that mannitol is preferable to glycerol as a tonicity modifier as the compositions in the presence of glycerol showed signs of precipitation following incubation at 50° C. for 6 weeks.

TABLE 13

Visual assessment of aqueous compositions produced of glucagon following incubation at 50° C. Extent of visible precipitation graded on a scale 1-3; 1 = clear solution; 3 = significant precipitation; * = gel formation.

| | Visual assessment (50° C. incubation) | | |
|---|---|---|---|
| Tonicity modifier | 0 days | 6 days | 6 weeks |
| Mannitol (250 mM) | 1 | 1 | 1 |
| Glycerol (250 mM) | 1 | 1 | 2 |
| Glycerol (800 mM) | 1 | 1 | 2 |
| Glycerol (2000 mM) | 1 | 1 | 2 |

In another experiment, the effects of mannitol and trehalose as tonicity modifiers were compared at 50° C. The background formulation contained 5 mM acetate, 5 mM methionine, and 0.075% benzethonium chloride, and was adjusted to pH 5.5. The results are shown in Table 14. The glucagon compositions remained as a clear liquid on incubation at 50° C. for up to 6 weeks both in the presence of mannitol (250 and 500 mM) and in the presence of trehalose (250 and 500 mM).

TABLE 14

Visual assessment of aqueous compositions produced of glucagon following incubation at 50° C. Extent of visible precipitation graded on a scale 1-3; 1 = clear solution; 3 = significant precipitation; * = gel formation.

| Surfactant and Tonicity modifier | Visual assessment (50° C. incubation) | | | |
|---|---|---|---|---|
| | 0 weeks | 1 week | 4 weeks | 6 weeks |
| Mannitol (250 mM) | 1 | 1 | 1 | 1 |
| Mannitol (500 mM) | 1 | 1 | 1 | 1 |
| Trehalose (250 mM) | 1 | 1 | 1 | 1 |
| Trehalose (500 mM) | 1 | 1 | 1 | 1 |

Example 6

Investigation of the Effect of Phenol, as Additional Excipient, Solubility of Glucagon Purpose of the Experiment The purpose of this experiment was to assess the effect of phenol as an additional excipient on the solubility and subsequent stability of glucagon in the presence of benzethonium chloride and other selected formulation components.

Experimental Procedure

Solution of glucagon (1 mg/ml) was prepared m a formulation containing 5 mM acetate (buffer), 0.075% (w/v) benzethonium chloride, 250 mM mannitol (tonicity modifier), 1.3 mM butylated hydroxytoluene (antioxidant), both in the presence and in the absence of 30 mM phenol. The pH of both formulations was adjusted to 5.5. For comparison, an composition representing reconstituted form of the currently marketed glucagon product was also prepared—this composition contained 1 mg/ml glucagon, 130 mM glycerol, 143 mM lactose (pH 2). The appearance of all formulations was noted shortly after preparation and then following storage at 50° C. for specified periods of time.

Results and Conclusion

The aqueous glucagon composition representing reconstituted form of the currently marketed glucagon product showed a rapid gel formation on incubation at 50° C. The gel formation and/or aggregation was delayed in both benzethonium-based formulations (i.e., both with and without phenol). However, the presence of phenol in liquid glucagon composition containing benzethonium chloride was shown to delay aggregation and gel formation considerably farther compared with the same formulation in the absence of phenol (Table 15).

TABLE 15

Visual assessment of aqueous compositions produced of glucagon following incubation at 50° C. Extent of visible precipitation graded on a scale 1-3; 1 = clear solution; 3 = significant precipitation; * = gel formation.

| Formulation | Visual assessment (50° C. incubation) | | | | |
|---|---|---|---|---|---|
| | 0 days | 3 days | 6 days | 12 days | 4 weeks |
| Lactose (143 mM), glycerol (130 mM), pH 2.5 | 1 | 1* | 1* | 1* | 1* |
| Acetate (5 mM), benzethonium chloride (0.075% w/v), mannitol (250 mM), butylated hydroxytoluene (1.3 mM), phenol (30 mM) | 1 | 1 | 1 | 1 | 1 |
| Acetate (5 mM), benzethonium chloride (0.075%, w/v), mannitol (250 mM), butylated hydroxytoluene (1.3 mM) | 1 | 2 | 2 | 1* | 1* |

Example 7

Investigation of the Stability of Formulations at pH in the Range 6-6.6

Purpose of the Experiment

The purpose of this experiment was to assess the stability of formulations of glucagon containing benzethonium chloride, trehalose and phenol, at pH in the range 6-6.6, by means of visual assessment upon preparation and after storage.

Experimental Procedure

Liquid formulations of glucagon (1 mg/ml) according to Table 16 were prepared, each containing 5 mM acetate (buffer), 0.2% (w/v) benzethonium chloride, 20 mM phenol, trehalose (at the specified concentration) as tonicity modifier and in some cases 1,2-propanediol (at the specified concentration) as an additional tonicity modifier. In some cases methionine (at the specified concentration) was included in the formulation as an antioxidant. The pH of each formulation was adjusted to the specified pH in the range 6.0-6.6. The appearance of all formulations was noted shortly after preparation and then following storage at 5, 25, 30, 35, 40° C. for 12 weeks.

TABLE 16

Formulations of glucagon at pH in the range 6-6.6.

| Trehalose (mM) | 1,2-Propane diol (mM) | Methionone (mM) | pH |
|---|---|---|---|
| 225 | 75 | 2 | 6.0 |
| 150 | 150 | 2 | 6.6 |
| 225 | 75 | 2 | 6.5 |
| 300 | 0 | 2 | 6.6 |
| 225 | 75 | 0 | 6.6 |
| 225 | 75 | 0* | 6.6 |
| 225 | 75 | 10 | 6.6 |

*stored in a sealed vessel under nitrogen

Results and Conclusion

By visual assessment, all formulations were clear solutions upon preparation and remained as clear solutions after 12 weeks storage at all temperatures studied. No signs of visible precipitation, fibril formation or gelling was observed in any of the formulations. The results indicate the suitability of pH in range 6-6.6 to stabilise certain formulations of glucagon. The inventors believe that these results can be extrapolated to indicate the suitability of pH in the range 6-7, although a range of 6-6.7 is expected to be preferred.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The disclosure of all patents, patent applications and publications identified in this specification are herein incorporated in their entirety by reference.

The invention embraces all combinations of preferred and more preferred groups and suitable and more suitable groups and embodiments of groups recited above.

What is claimed is:

1. An aqueous solution composition having pH between 5 and 7 comprising (i) glucagon having the sequence of SEQ ID NO:1, at a concentration of 0.05 to 0.2% w/v, (ii) benzethonium chloride as a solubilising agent at a concentration of 0.05 to 0.2% w/v, and (iii) an uncharged tonicity modifying agent at a concentration of 50 to 500 mM or mixture of uncharged tonicity modifying agents at a concentration of 50 to 500 mM, wherein the overall concentration of charged species, other than those originating from glucagon and benzethonium chloride, in the composition is at least 2 mM and less than 25 mM.

2. The composition according to claim 1 wherein the concentration of the benzethonium chloride is 0.15 to 0.20% w/v.

3. The composition according to claim 1 which additionally comprises phenol at a concentration of 1-50 mM.

4. The composition according to claim 1 wherein the pH is 5 to 6.

5. The composition according to claim 1 wherein the pH is 6.1 to 7.

6. The composition according to claim 1 containing glucagon at a concentration of 0.1 to 0.2% w/v.

7. The composition according to claim 1 wherein the ratio of concentration of glucagon/benzethonium chloride expressed as w/v is greater than 7/1.

8. The composition according to claim 1 which is substantially free of a non-ionic surfactant.

9. The composition according to claim 1 which is substantially free of ionic detergents including anionic, cationic and zwitterionic surfactants apart from benzethonium chloride.

10. The composition according to claim 1 further comprising a polyol selected from 1,2-propanediol, glycerol, mannitol, sorbitol, xylitol, lactitol, sucrose, raffinose and trehalose.

11. The composition according to claim 10 wherein the polyol is mannitol, trehalose or a mixture thereof.

12. The composition according to claim 10 wherein the polyol is a mixture of trehalose and 1,2-propanediol.

13. The composition according to claim 1 which comprises acetate as a buffer.

14. The composition according to claim 1 having a pH around 5.5, comprising glucagon, benzethonium chloride as cationic surfactant, mannitol as tonicity modifying agent and acetate as buffer.

15. The composition according to claim 14 which additionally comprises methionine, phenol, or a mixture thereof.

16. The composition according to claim 1 with a pH in the range 6.4 to 6.6, comprising glucagon, benzethonium chloride, trehalose as a tonicity modifying agent optionally in combination with 1,2-propanediol, phenol and acetate as a buffer.

17. The composition according to claim 16, which additionally comprises methionine as antioxidant.

18. A container containing a unit dose of the composition according to claim 1.

19. A single-use injector for intramuscular, sub-cutaneous or parenteral administration comprising injection apparatus and a container containing a unit dose of the composition according to claim 1 to be injected.

20. A pump device comprising a container in fluid communication with a needle containing a unit dose of the composition according to claim 1 to be injected or infused.

* * * * *

SEQUENCE LISTING

<160> NUMBER OF SEQ ID NOS: 1

<210> SEQ ID NO 1
<211> LENGTH: 29
<212> TYPE: PRT
<213> ORGANISM: Artificial Sequence
<220> FEATURE:
<223> OTHER INFORMATION: glucagon

<400> SEQUENCE: 1

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```